US 6,699,719 B2

(12) United States Patent
Yamazaki et al.

(10) Patent No.: US 6,699,719 B2
(45) Date of Patent: Mar. 2, 2004

(54) BIOSENSOR ARRAYS AND METHODS

(75) Inventors: Miki (Vikky) Yamazaki, Redwood Shores, CA (US); Morrison Ulman, Mountain View, CA (US); Luat T. Nguyen, Fremont, CA (US); Steven G. Boxer, Stanford, CA (US); John T. Groves, Berkeley, CA (US)

(73) Assignee: Proteomic Systems, Inc., Sunnyvale, CA (US)

( * ) Notice: Subject to any disclaimer, the term of this patent is extended or adjusted under 35 U.S.C. 154(b) by 0 days.

(21) Appl. No.: 10/200,682

(22) Filed: Jul. 22, 2002

(65) Prior Publication Data

US 2003/0096418 A1 May 22, 2003

Related U.S. Application Data

(63) Continuation-in-part of application No. 09/631,906, filed on Aug. 4, 2000, now Pat. No. 6,503,452, which is a continuation-in-part of application No. 08/978,756, filed on Nov. 26, 1997, now Pat. No. 6,228,326.
(60) Provisional application No. 60/032,325, filed on Nov. 29, 1996, provisional application No. 60/205,604, filed on May 18, 2000, and provisional application No. 60/158,485, filed on Oct. 8, 1999.

(51) Int. Cl.[7] .............................................. G01N 27/12
(52) U.S. Cl. .................... 436/71; 436/164; 436/172; 422/82.02; 422/82.06; 427/2.13
(58) Field of Search ............... 422/68.1, 82.02, 422/82.06; 436/71, 525, 527, 528, 164, 172; 435/287.2, 287.1; 427/2.11, 2.13

(56) References Cited

U.S. PATENT DOCUMENTS

| | | | | |
|---|---|---|---|---|
| 4,634,599 A | * | 1/1987 | Uzgiris | 427/2.13 |
| 5,192,507 A | * | 3/1993 | Taylor et al. | 422/68.1 |
| 5,204,239 A | * | 4/1993 | Gitler et al. | 435/7.1 |
| 5,234,566 A | * | 8/1993 | Osman et al. | 204/403.06 |
| 5,328,847 A | * | 7/1994 | Case et al. | 205/778 |
| 5,368,712 A | * | 11/1994 | Tomich et al. | 204/403.06 |
| 5,401,378 A | * | 3/1995 | King et al. | 205/778 |
| 5,494,803 A | * | 2/1996 | Carbonell et al. | 435/7.92 |
| 5,731,152 A | * | 3/1998 | Maracas et al. | 435/6 |
| 5,756,355 A | * | 5/1998 | Lang et al. | 435/7.21 |
| 5,807,522 A | * | 9/1998 | Brown et al. | 422/50 |
| 5,837,860 A | * | 11/1998 | Anderson et al. | 536/25.3 |
| 5,843,767 A | * | 12/1998 | Beattie | 435/287.1 |
| 5,846,814 A | * | 12/1998 | Galla et al. | 435/287.2 |
| 5,922,594 A | * | 7/1999 | Lof.ang.s | 435/278.1 |
| 6,001,556 A | * | 12/1999 | Charych et al. | 435/5 |

OTHER PUBLICATIONS

Alon, R. et al., "Lifetime of the P–selectin–carbohydrate bond and its response to tensile force in hydrodynamic flow", Nature, 1995, 374:539–542.

(List continued on next page.)

Primary Examiner—Jeffrey Snay
(74) Attorney, Agent, or Firm—Bingham McCutchen LLP

(57) ABSTRACT

A surface detector array device suitable for use with a biosensor is disclosed. The device is formed of a substrate having a surface defining a plurality of distinct bilayer-compatible surface regions separated by one or more bilayer barrier regions. The bilayer-compatible surface regions carry on them, separated by a film of aqueous, supported fluid bilayers. The bilayers may contain selected receptors or biomolecules. A bulk aqueous phase covers the bilayers on the substrate surface. Multiplexed assays using the surface detector array device of the present invention are disclosed, as are automated methods for making the surface detector array device that enable formation of arrays wherein the composition of the individual, addressable bilayer regions is unrestricted.

34 Claims, 11 Drawing Sheets

(5 of 11 Drawing Sheet(s) Filed in Color)

OTHER PUBLICATIONS

Bayley, H. et al., "Stochastic sensors inspired by biology", *Nature*, 2001, 413:226–230.

Bieri, C. et al., "Micropatterned immobilization of a G protein–coupled receptor and direct detection of G protein activation", *Nature Biotech.*, 1999, 17:1105–1108.

Brian, A.A. et al., "Allogenic stimulation of cytoxic T cells by supported planar membranes", *Proc Natl. Acad. Sci. USA*, 1984, 81:6159–6163.

Closse, C., "Phosphatidylserine–related adhesion of human erthrocytes to vascular endothelium", *British J. Haematology*, 1999, 107:300–302.

Cremer, P.S. et al., "Creating spatially addressed arrays of planar supported fluid phospholipid membranes", *J. Am. Chem. Soc.*, 1999, 121:p. 8130–8131.

Dietrich, C. et al., "Lipid rafts reconstructed into model membranes", *Biophys. J.*, 2001, 80: p. 1471–1428.

Fang, Y. et al., "Membrane Protein Microarrays", *J. Am. Chem. Soc.*, 2002, 124(11):2394–2395.

Finger, E. B. et al., "Adhesion through L–selectin requires a threshold hydrodynamic shear", *Nature*, 1996, 379:266–269.

Fodor, S.P.A., et al, "Light–directed, spatially addressable parallel chemical synthesis", *Science*, 1991, 251:767–773.

Grakoui, A. et al., "The immunological synapse: A molecular machine controlling T cell activation." *Science*, 1999, 285: pp. 221–227.

Groves, J. T. et al., "Micropattern formation in supported lipid membranes." *Acc. Chem. Res.*, 2002, 35:149–157.

Groves, J. T. et al., "Electric Field–Induced Concentration Gradients in Planar Supported Bilayers" *Biophysical Journal*, 1995, 69:1972–1975.

Groves, J. T. et al., "Electrical Manipulation of Glycan–Phosphatidyl Inositol Tethered Proteins in Planar Supported Bilayers", *Biophysical Journal*, 1996, 71:2716–2723.

Groves, J. T. et al., "Control of cell adhesion and growth with micropatterned supported lipid membranes", *Langmuir*, 2001, 17(17):5129–5133.

Groves, J. T. et al., "Micropatterning fluid lipid bilayers on solid supports", *Science*, 1997, 275:651–653.

Haga, T. et al., "G–protein coupled receptors", 1999, CRC Press: Boca Raton.

Hovis, J. S. et al., "Patterned barriers to lateral diffusion in supported lipid bilayer membranes by blotting and stamping", *Langmuir*, 2000, 16:894–897.

Hovis, J. S. et al., "Patterning and composition arrays of supported lipid bilayers by microcontact printing", *Langmuir*, 2001, 17:3400–3405.

Kam, L. et al., "Formation of supported lipid bilayer composition arrays by controlled mixing and surface capture",*J. Am. Chem. Soc.*, 2000, 122:12901–12902.

Karlsson, O.P., et al., "Flow–mediated on–surface reconstitution of G–protein coupled receptors for applications in surface plasmon resonance biosensors", *Anal. Biochem.*, 2002, 300:132–138.

Kiessling, L. L. et al., "Synthetic multivalent ligands in the exploration of cell–surface interactions", *Curr. Op. Chem. Biol.*, 2000, 4:606–703.

Kodadek, T., "Protein microarrays: prospects and problems", *Chemistry & Biology 8*, 2001, 105–115.

Kukar, T. et al., "Protein Microarrays to Detect Protein–Protein Interactions Using Red and Green Fluorescent Proteins", *Analytical Biochemistry*, 2002, 306:50–54.

Kung, L. et al., "Printing via photolithography on micropartitioned fluid lipid membranes", *Adv. Mater.*, 2000, 12(10): pp. 731–734.

Kung, L. A. et al., "Printing via Photolithography on Micropartitioned Fluid Lipid Membranes", *Adv. Mater.*, 2000, 12: pp. 731–734.

Kung, L. A. et al., "Patterning hybrid surfaces of proteins and supported lipid bilayers", *Langmuir*, 2000, 16:6773–6776.

Lawrence, M. B. et al., "Leukocytes roll on a selectin at physiological flow rates: distinction from and prerequisite for adhesion through integrins", *Cell*, 1991, 65:859–873.

Macbeath, G., "Protein microaarays and proteomics", *Nature Genetics Supplement*, 2002, 32:526–532.

Macbeath, G., "Proteomics comes to the surface", *Nature Biotechnology*, 2001, 19:828–829.

Macbeath, G. et al., "Printing proteins as microarrays for high–throughput function determination", *Science*, 2000, 289:1760–1763.

Mammen, M. et al., "Polyvalent interactions in biological systems: implications for design and use of multivalent ligands and inhibitors", *Angew. Chem. Int. Ed.*, 1998, 37:2754–2794.

McConnell, H. M. et al., "Supported planar membranes in studies of cell–cell recognition in the immune system", *Biochim. Biophys. Acta*, 1986, 864: pp. 95–106.

Mitchell, P. "A perspective on protein arrays", *Nature Biotech.*, 2002, 20: pp. 225–229.

Rädler, J. et al., "Phenomenology and kinetics of lipid bilayer spreading on hydrophilic surfaces", *Langmuir*, 1995, 11: pp. 4539–4548.

Renault, J. P. et al., "Fabricating Microarrays of Functional Proteins Using Affinity Contact Printing",*Angew. Chem. Int. Ed.*, 2002, 41:1433.

Sackmann, E. et al., "Supported membranes on soft polymer cusions: fabrication, characterization, and applications", *Tibtech*, 2000, 18:58–64.

Sackmann, E., "Support membranes: Scientific and practical applications", *Science*, 1996, 271:43–48.

Salafsky, J. et al., "Architecture and function of membrane proteins in planar supported bilayers: a study with photosynthetic reaction centers", *Biochemistry*, 1996, 35:14773–14781.

Schweitzer, B. et al., "Measuring proteins on microarrays", *Current Opinion in Biotechnology*, 2002, 13:14–19.

Sheets, E. D. et al., "Membrane organization in immunoglobulin E receptor signaling." *Curr. Opin. Chem. Biol.*, 1999, 3:95–99.

Simmons, K. et al., "Functional rafts in cell membranes", *Nature*, 1997, 387:569–572.

Stelzle, M. et al., "On the Application of Supported Bilayers as Receptive Layers for Biosensors with Electrical Detection", *J. Phys. Chem.*, 1993, 97:2974–2981.

Stelzle, M. et al., "Sensitive detection of protein adsorption to supported lipid bilayers by frequency–dependant capacitance measurements and microelectrophoresis", *Biochimica et Biophysica Acta*, 1989, 981:135–142.

Sui, S. et al., "Interaction of Insulin Receptors with Lipid Bilayers and Specific and Nonspecific Binding of Insulin to Supported Membranes", *Biochemistry*, 1988, 27:7463–7469.

Tamm, L. K. et al., "Microspectrofluoremetry of supported planar membranes, in Molecular luminescence spectroscopy," S. G. Schulman, Editor., 1993, John Wiley & Sons, Inc., 253–305.

Tamm, L. K. et al., "Supported phospholipid bilayers." Biophys. J., 1985, 47:105–113.

Thompson, N. L., et al., "Dynamics of antibodies on planar model membranes", *Acc. Chem. Res.*, 1993, 11:567–573.

Wagner, P. et al., "Protein biochips: an emerging tool for proteomics research", *Current Drug Discovery*, 2002, 23–28.

Wali, R. K. et al., "Alterations in organization of phospholipids in erythrocytes as factor in adherence to endothelial cells in diabetes mellitus." *Diabetes*, 1988, 37(1):104–111.

Wong, A. P., "Topographical Imaging of an Intermembrane Junction by Combined Fluorescence Interference and Energy Transfer Microscopies", *J. Am. Chem. Soc.*, 2001, 123:12414–12415.

Yang, T. et al., "Creating Addressable Aqueous Microcompartments above Solid Supported Phospholipid Bilayers Using Lithography Patterned Poly(dimethysiloxane) Molds", *Anal. Chem.*, 2000, 72:2587–2589.

Yang, T. et al., "Fabrication of phospholipid bilayer–coated microchannels for on–chip immunoassays", *Anal. Chem.*, 2001, 73:165–169.

Zhu, H. ET AL., "Global Analysis of Protein Activities Using Proteome Chips", *Science*, 2001, 293:2102–2105.

Zhu, H. et al., "Protein chip technology", *Current Opinion in Chemical Biology*, 2003, 293:2101–2105.

Ziauddin, J. and D. M. Sabatini: "Microarrays of cells expressing defined cDNAs", *Nature*, 2001, 411:107–110.

Ziauddin, J. et al., "Microarrays of cells expressing defined cDNAs", *Nature*, 2001, 411:107–110.

\* cited by examiner

BIOSENSOR ARRAYS AND METHODS

CROSS-REFERENCE TO RELATED APPLICATIONS

This application is a continuation-in-part of U.S. patent application Ser. No. 09/631,906 filed Aug. 4, 2000, now U.S. Pat. No. 6,503,452 which application is a continuation-in-part of U.S. patent application Ser. No. 08/978,756 filed Nov. 26, 1997, now U.S. Pat. No. 6,228,326 which claims priority of U.S. Provisional application Serial No. 60/032,325 filed Nov. 29, 1996, each of which is entirely incorporated herein by reference.

This application is further related to U.S. Provisional applications No. 60/205,604, filed May 18, 2000, and No. 60/158,485, filed Oct. 8, 1999, both of which are entirely incorporated herein by reference.

FIELD OF THE INVENTION

The present invention relates in general to supported fluid bilayers and methods of confining them to selected areas. More specifically, the invention relates to microfabricated arrays of independently-addressable supported fluid bilayer membranes, their uses, and methods for their manufacture.

STATEMENT REGARDING FEDERALLY SPONSORED RESEARCH

Not applicable.

BACKGROUND OF THE INVENTION

Over the last several years, a number of high-throughput screening methods have been developed to facilitate the screening of thousands, if not millions, of compounds for a desired activity or activities. Such methods are typically based on detecting the binding of a potentially effective compound to a receptor. While these binding assays are effective at constraining the universe of compounds which may have the desired activity, they are typically not well-suited for evaluating this activity with any degree of detail.

The biological activity of potentially active compounds is typically evaluated using less efficient but more informative "secondary screens" or assays which typically require a substantial input of time by a trained technician or scientist. For evaluation of candidate compounds affecting integral membrane proteins such as receptors and ion channels, the amount of time required per compound may be several hours or days if the assay includes effects on electrophysiological activity. Accordingly, there is a need for a more efficient "secondary screen" of compounds affecting the activity of such integral membrane proteins and other membrane or membrane-associated components, to identify those few compounds that justify further detailed analysis.

BRIEF SUMMARY OF THE INVENTION

In one aspect, the present invention includes a surface detector array device. The device includes a substrate having a surface defining a plurality of distinct bilayer-compatible surface regions separated by one or more bilayer barrier regions, a bulk aqueous phase covering the substrate surface, a lipid bilayer expanse carried on each of the bilayer-compatible surface regions, and an aqueous film interposed between each bilayer-compatible surface region and corresponding lipid bilayer expanse. In a general preferred embodiment, the bilayer-compatible surface regions and the bilayer barrier surface regions are formed of different materials.

The bilayer-compatible surface region may be formed from any of a variety of materials having such bilayer-compatible surface properties, including $SiO_2$, $MgF_2$, $CaF_2$, and mica, as well as a polymer film, such as a polyacrylamide or dextran film. $SiO_2$ is a particularly effective material for the formation of a bilayer-compatible surface region.

The bilayer barrier surface region may be formed from any of a variety of materials having such bilayer barrier surface properties, including gold, positive photoresist, aluminum oxide, and indium tin oxide.

In a general embodiment, the lipid bilayer expanse contains at least one lipid selected from the group consisting of phosphatidylcholine, phosphatidylethanolamine, phosphatidylserine, phosphatidic acid, phosphatidylinositol, phosphatidylglycerol, and sphingomyelin.

In one embodiment, the device contains between about 10 and about 100 distinct bilayer-compatible surface regions. In another embodiment, the device contains at least about 2500 distinct bilayer-compatible surface regions. In yet another embodiment, the device contains at least about 25,000 distinct bilayer-compatible surface regions. In still another embodiment, the device contains at least about 2.5 million distinct bilayer-compatible surface regions.

The bilayer-compatible surface regions are separated from one another, in one general, embodiment, by bilayer barrier regions that are between about 1 $\mu$m and about 10 $\mu$m in width.

The lipid bilayer expanses on different bilayer-compatible surface regions may have different compositions, and may further include a selected biomolecule, with different expanses having a different biomolecule, such as a transmembrane receptor or ion channel. The biomolecule may be covalently or non-covalently attached to a lipid molecule. Examples of non-covalent interactions include electrostatic and specific molecular interactions, such as biotin/streptavidin interactions. Examples of biomolecules include proteins, such as ligands and receptors, as well as polynucleotides and other organic compounds.

In another aspect, the invention includes a method of forming a surface detector device having a plurality of independently-addressable lipid bilayer regions. The method includes the steps of (i) treating a planar substrate to form a substrate surface defining a plurality of distinct bilayer-compatible surface regions separated by one or more bilayer barrier regions, and (ii) applying a suspension of lipid bilayer vesicles to the plurality of distinct bilayer-compatible surface regions under conditions favorable to the formation of supported bilayers on the bilayer-compatible surface regions. The applying of the vesicles results in the formation of supported bilayer membranes on the bilayer-compatible surface regions.

In another aspect, the invention includes a method of forming a surface detector array device. The method includes the steps of (i) providing a substrate having a surface defining a plurality of distinct bilayer-compatible surface regions separated by one or more bilayer barrier regions, (ii) applying a first suspension of lipid bilayer vesicles having a first composition to a first of said plurality of distinct bilayer-compatible surface regions, (iii) applying a second suspension of lipid bilayer vesicles having a second composition to a second of said plurality of distinct bilayer-compatible surface regions, (iv) incubating the substrate with the first and second suspensions to form a first lipid bilayer expanse stably localized above the first distinct bilayer-compatible surface region and a second lipid bilayer expanse stably localized above the second distinct bilayer compatible surface region, and (v) establishing a bulk aqueous phase above the lipid bilayer expanses.

In a preferred embodiment, the applying steps of the above-described method comprise generating drops of the first and/or second suspensions on an end of a transfer device such as, e.g., a hollow ceramic tip, a hollow metal tip, a micropipette, a pin, or the like, and touching the drops to the first and second bilayer-compatible region(s). In certain embodiments, the drops comprise less than 100 nl, less than 75 nl, less than 50 nl, less than 25 nl, less than 15 nl, less than 10 nl, or less than 5 nl.

In another preferred embodiment, the applying steps of the above-described method comprise ejecting aliquots of the first and/or second suspensions from an end of a transfer device such as, e.g., a hollow ceramic tip, hollow metal tip, micropipette, an electro-piezo print head, an ink-jet print head or the like, across an air space separating the end of the transfer device from the bilayer-compatible surface regions, and onto the bilayer compatible surface region(s). In certain embodiments, the ejected aliquots comprise less than 100 nl, less than 75 nl, less than 50 nl, less than 25 nl, less than 15 nl, less than 10 nl, or less than 5 nl.

In yet another aspect, the invention includes a method for detecting a selected ligand in a mixture of ligands. The method includes the steps of (i) contacting the mixture with a biosensor surface detector array device such as described above, and (ii) detecting binding of the selected ligand to receptors which specifically bind it.

In another aspect, the invention includes a method for assaying the interaction between a test agent and a composition. The method includes the steps of (i) providing a biosensor surface detector array device such as described above, wherein said device comprises a first lipid bilayer expanse having a first composition and a second lipid bilayer expanse having a second composition different from said first composition, (ii) contacting the device with a bulk aqueous phase comprising a test agent, and (iii) assaying an interaction between the test agent and the first composition and between the test agent and the second composition.

In preferred embodiments, the lipid bilayer expanses each comprise less than 5 $\mu$g of material, or less than 1 $\mu$g of material, or less than 0.5 $\mu$g of material.

In other preferred embodiments, the first composition comprises a first biomolecule and the second composition comprises a second biomolecule. In another preferred embodiment, the first and second biomolecules are different members of a receptor protein family. In yet another preferred embodiment, the first and second compositions comprise different lipids.

In still another aspect, the invention includes a surface detection array device for use in a biosensor. Such a device includes (i) a substrate having a surface defining a plurality of distinct bilayer-compatible surface regions separated by one or more bilayer barrier regions, (ii) a bulk aqueous phase covering the substrate surface, (iii) a lipid bilayer expanse carried on each of the bilayer-compatible surface regions, and (iv) an aqueous film interposed between each bilayer-compatible surface region and corresponding lipid bilayer expanse. Each bilayer expanse contains a specie of receptor, or biomolecule, and different bilayer expanses contain different species of receptors or biomolecules.

Another aspect of the present invention provides for a surface detector array device, comprising a substrate having a surface defining a plurality of distinct bilayer-compatible surface regions separated by one or more bilayer barrier regions, a bulk aqueous phase covering said substrate surface, a lipid bilayer expanse carried on each of said bilayer-compatible surface regions, and an aqueous film interposed between each bilayer-compatible surface region and corresponding lipid bilayer expanse, wherein said bilayer-compatible surface regions and said bilayer barrier surface regions are formed of different materials, and wherein each bilayer-expanse carried on each bilayer-compatible region is compositionally different than adjacent bilayer-expanses. Other embodiments of the invention further include a plurality of groups of said bilayer-compatible regions, wherein said groups each define an area where said bilayer-expanses are compositionally similar, and where the bilayer-expanses within different groups are compositionally different.

The invention further provides a method for forming an array of biosensor regions, where each region has a different, known lipid bilayer compositions comprising the steps of:

providing a biosensor array having a plurality of lipid bilayer compatible regions, each compatible region being surrounded by one or more bilayer barrier regions, providing a gradient forming device loaded with two or more different lipid bilayer compositions, the gradient forming device in fluid communication with a spot forming device for forming spots on a surface, providing a multi-axis translation table for holding and translating a biosensor array workpiece, placing a biosensor array workpiece that has a plurality of bilayer compatible regions surrounded by one or more barrier regions, and forming spots of mixed lipid bilayer compositions resulting from the gradient forming device forming a gradient and translating the table in at least one axis while dispensing such composition mixture as it is formed thereby dispensing to different, consecutive locations different ratios of each lipid bilayer compositions.

The invention further provides a method for making gradient biosensor array comprising the steps of: mixing together first and second different lipid bilayer forming compositions contained from first and second sources by flowing in a substantially laminar flow, two different compositions from two different sources into one mixing chamber that substantially retains the laminar flow character of the two different compositions while flowing through the mixing chamber, where the facing edges of each different composition mix to form a gradient having a first edge and a second edge and further comprising composition combinations of different ratios beginning from the first edge of the gradient that faces the first composition, and ending at the second edge of the gradient that faces the other, second composition, and where the mixing chamber is adapted to dispense the gradient in a substantially laminar flow across the surface of the array, and where the compositions contained in the gradient are captured and retained upon initial contact by bilayer-compatible regions of the array.

These and other objects and features of the invention will become more fully apparent when the following detailed description is read in conjunction with the accompanying drawings.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF THE PREFERRED EMBODIMENTS

I. Definitions

Figure 1:
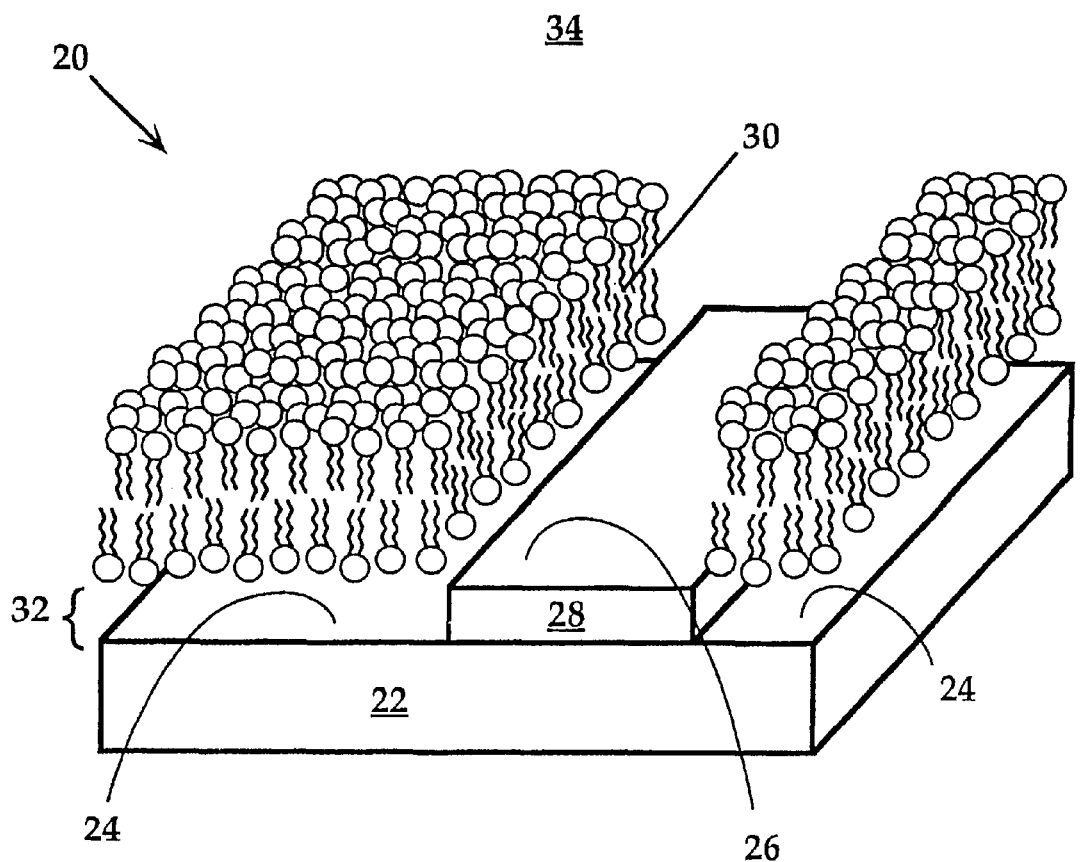
FIG. 1 shows a portion of a surface detector array device (SDAD) of the invention.

All terms, unless specifically defined below, are intended to have their ordinary meanings as understood by those of skill in the art. Claimed masses and volumes are intended to encompass variations in the stated quantities compatible with the practice of the invention. Such variations are contemplated to be within, e.g., about ±10–20 percent of the stated quantities. In case of conflict between the specific definitions contained in this section and the ordinary meanings as understood by those of skill in the art, the definitions supplied below are to control.

The term "aqueous" refers to a water-based liquid medium that is not deleterious to lipids.

A "receptor" is a macromolecule capable of specifically interacting with a ligand molecule. In cells, receptors are typically associated with lipid bilayer membranes, such as the extracellular, Golgi or nuclear membranes. Receptors for incorporation into expanses of lipids in vitro (e.g., supported bilayers) may either be purified from cells, recombinantly expressed, or, in the case of small receptors, chemically synthesized.

A "ligand" is a molecule capable of specifically binding to a receptor. Binding of the ligand to the receptor is typically characterized by a high binding affinity, i.e., $K_a > 10^5$, and can be detected either as a change in the receptor's function (e.g., the opening of an ion channel associated with or part of the receptor) or as a change in the immediate environment of the receptor (e.g., detection of binding by surface plasmon resonance). Ligands for incorporation into expanses of lipids in vitro (e.g., supported bilayers) may either be purified from cells, recombinantly expressed, or, in the case of small ligands, chemically synthesized.

Binding is "specific" if it results from a molecular interaction between a binding site on a receptor and a ligand, rather than from "non-specific" sticking of a ligand to a receptor. In cases where the ligand binds the receptor in a reversible manner, specificity of binding can be confirmed by competing off labeled ligand with an excess of unlabeled ligand according to known methods. Non-specific interactions can be minimized by including an excess of a protein (e.g., BSA) that does not have binding sites for either the ligand or receptor.

A "fluid membrane" is a membrane having a native or native-like bilayer structure. As one of ordinary skill will recognize, some "fluid membranes" (i.e., those having high proportions of saturated lipids and/or sterols) may not have appreciable fluidity, yet nonetheless will be considered to be "fluid membranes" for purposes of the present invention.

A "lipid bilayer vesicle" is a vesicle capable of fusing to a bilayer-compatible surface region of the surface detector array devices of the present invention to form a "fluid membrane." A "lipid bilayer vesicle" may optionally contain, in addition to the lipid components, other membrane-associated components such as proteins (such vesicles referred to herein as "proteovesicles" or "proteoliposomes"), glycoproteins, glycolipids, etc.

"Assaying an interaction between a test agent and a composition" means determining whether the test agent interacts with the composition. "Assaying an interaction between a test agent and a composition" may be done by detecting interaction of a test agent with a composition using any method now known to one of skill in the art, or later developed, and is intended to encompass binding assays, such as direct binding and displacement assays, electrophysiological assays, metabolic assays, etc.

A "test agent" is intended to encompass all manner of organic, inorganic, biological and non-biological molecules that may be used in conjunction with the methods of the present invention.

A "transmembrane receptor" is an integral membrane protein that, when present in a cell membrane, transduces a binding event occurring on the extracellular side of the membrane into an intracellular signal.

"Members of a receptor protein family" refers to two or more proteins that are related in structure and/or function within or between organisms. Determining that proteins are "members of a receptor protein family" may be done using computerized algorithms known to persons of skill in the art to carry out, e.g., primary, secondary, tertiary, or quaternary structure alignments. Representative algorithms such as BLAST and VAST may be obtained from the Computational Biology Branch, National Center for Biotechnology Information, National Institutes of Health, 8600 Rockville Pike, Bethesda, Md. 20894 USA, and may be run directly from the National Center for Biotechnology Information website, www.ncbi.nlm.nih.gov.

"Transferring an aliquot" means separating a portion of a bulk liquid from the bulk liquid and transferring said separated portion to another location. Transferring an aliquot may be accomplished using any fluid transfer device now known to one of ordinary skill in the art or later developed such as, e.g., a hollow ceramic tip, a hollow metal tip, a micropipette, a pin, an electro-piezo print head, an ink-jet print head, or the like. "Transferring an aliquot" is not intended to encompass the laminar flow gradient methods described herein, wherein bulk solutions are mixed and transferred, en masse, to the surface detector array device substrate.

II. Surface Detector Array Device

FIG. 1 is a perspective view of a portion of a surface detector array device (SDAD) 20 in accordance with the invention. The device is fabricated from a substrate 22, such as an oxidized silicon or fused silica wafer. The dimensions of the substrate are typically between about 0.1 cm to about 10 cm per side and about 0.01 mm to about 1 cm in thickness.

The substrate surface contains a plurality of distinct bilayer-compatible surface regions 24 separated by one or more bilayer barrier regions 26. The bilayer barrier region(s) 26 are preferably formed of a material 28 different from the material 22 forming the bilayer-compatible surface regions 24.

A lipid bilayer expanse 30 is carried on each of the bilayer-compatible surface regions 24. Interposed between each bilayer-compatible surface region 24 and corresponding lipid bilayer expanse 30 is an aqueous film 32 that is between about 5 Å and 15 Å (typically about 10 Å) in thickness. In some configurations, separation of up to 1 micron can be achieved (Wong & Groves, 2001 incorporated herein by reference). Covering the substrate surface and lipid expanses is a bulk aqueous phase 34.

The bilayer barrier regions may be depressed, flush, or elevated (as shown at 26 in FIG. 1), with respect to the bilayer-compatible surface 24. In embodiments having elevated barriers, the height of the barrier may range from tens of Angstroms to several micrometers or more. The width of the barriers is typically between about 100 nm and about 250 µm. Preferably, the width is between about 1 µm and 100 µm.

According to results of experiments performed in support of the invention, the lipid barrier regions do not function simply by mechanical or physical separation of adjacent lipid bilayer regions. Rather, the experiments indicate that the characteristics which allow a surface to act as a bilayer barrier region are chemical/electrostatic properties intrinsic to the material making up the surface. Examples of such chemical/electrostatic properties include hydrophobicity, dielectric permeability, conductivity, and surface charge density.

Similarly, the degree of "bilayer-compatibility" of a selected surface is a function of its intrinsic material properties rather than its shape. The interactions between membranes and surfaces involve electrostatic and hydration forces as well as attractive contributions from long-range van der Waals forces. In a suitable bilayer-compatible surface, an energetic minimum traps the bilayer membrane between about 5 Å and 15 Å (typically about 10 Å) away from the supporting surface, separated from the supporting surface by an aqueous film of corresponding thickness. Bilayer-compatible surfaces are typically hydrophilic.

Functionally, the suitability of a material for use as a bilayer barrier surface region or a bilayer-compatible surface region may be evaluated by the material's performance in a simple "fluorescence recovery after photobleaching" (FRAP) test as follows:

A small sample of the material (e.g., a portion having a ~1 cm² flat surface) is cleaned or treated as described herein (e.g., using exposure to argon plasma or, for materials which can tolerate it, an acid wash). The surface is then rinsed and a selected amount (e.g., 50 µl) of a suspension of lipid vesicles containing a fluorescent marker (prepared as described in the Materials and Methods) is applied to the surface. The suspension is allowed to remain in contact with the surface for several minutes (e.g., 5 min). The surface is then immersed in an aqueous medium to rinse off or substantially dilute the suspension (e.g., by adding ~100 ml of distilled water or PBS), and the surface is transferred to the stage of a standard fluorescence microscope. A portion of the surface is then exposed to a bright light (e.g., from a 100 W mercury arc lamp) sufficient to bleach the fluorescent moieties of the reporter exposed to the light (e.g., about 1 min., depending on the fluorophore), and the surface is monitored under the microscope for ~10 minutes (depending on size of the bleached spot) to assess recovery of fluorescence.

When the above test is carried out using a material capable of forming a bilayer-compatible surface, vesicles in the suspension will have fused with the surface forming a supported bilayer containing the fluorescent reporter, and the localized exposure to photobleaching light will have bleached the area of the bilayer corresponding to the region of the surface on which the photobleaching light was focused. During the monitoring period, fluorescence in the bleached area of the bilayer will recover due to the fluidity of the supported bilayer.

In contrast, when the above test is carried out using a material that forms a bilayer-barrier surface, vesicles in the suspension will not have fused with the surface to form a fluid bilayer. Under such conditions, the vesicles will either be rinsed off during the rinse step or will remain attached and immobilized on the surface. If the vesicles rinse off, little or no fluorescence will be observed. If the vesicles stick to the surface but do not form a fluid bilayer, fluorescence will not be recovered in the bleached area following photobleaching. In either case, the material is an effective bilayer barrier material. It will be appreciated, however, that the use of materials to which the vesicles do not stick is preferable to the use of those which, following the above FRAP test, contain immobilized lipid or membrane material.

The above test can be carried in parallel with a number of different materials that the practitioner of the invention may have at hand. In this way, in a matter of a few hours, the practitioner can readily determine whether a particular material will be effective to form a surface that is either bilayer-compatible or serves as a bilayer barrier.

It will be appreciated that essentially all materials suitable for use in the microfabrication of a device according to the invention will, when cleaned, present either a bilayer-compatible surface region or a bilayer-barrier surface region. Accordingly, application of the simple FRAP test described above will typically yield a material useful in the practice of the invention with each material tested.

Exemplary materials having properties making them suitable for lipid bilayer barriers include certain polymers (e.g., photoresist) and various metals (e.g., gold) and minerals (e.g., aluminum oxide and indium tin oxide). An advantage of photoresist is that it is relatively easy to pattern with a photomask and is nonconductive. Aluminum oxide has the advantage of being both nonconductive and reusable, withstanding most cleaning procedures.

Exemplary materials having properties making them suitable for bilayer-compatible surfaces include various glasses, silicon oxides, including oxidized silicon ($SiO_2$), $MgF_2$, $CaF_2$, mica, and various polymer films, such as thin polyacrylamide or dextran films (see, e.g., Elender, et al., 1996; Khuner, et al., 1994), both incorporated herein by reference). Both types of polymer films form a suitable bilayer-compatible surface that is hydrated to provide a film of aqueous between the polymer film and the supported bilayer membrane.

To generate a substrate surface that is "bilayer-compatible", the surface is typically cleaned and/or treated to remove surface impurities (dirt, oils, etc.). Suitable treatments are discussed below with respect to the making or construction of a device of the invention.

The supported bilayer itself is a self-assembling, two-dimensional fluid system, typically consisting of two opposed leaflets of vesicle-forming lipid molecules. The two opposed leaflets assemble with hydrophic tail groups directed to the interior of the bilayer and with hydrophilic head groups directed to the exterior of the bilayer in a native or native-like configuration. However, the supported bilayer can be constructed as described below from any suitable membrane-forming amphiphile, including proteins and non-lipids.

Most vesicle-forming lipids are long-chain carboxylic acids, such as glycerides, having the hydroxyl groups of the glycerol esterified with (i) fatty acid chain(s), and (ii) a charged or polar moiety, such as a phosphate-ester group. The vesicle-forming lipids are preferably ones having two hydrocarbon chains, typically acyl chains, and a polar head group. Long-chain carboxylic acids with a phosphate group, or phospholipids, are particularly well-suited for use with the present invention. There are a variety of synthetic vesicle-forming lipids and naturally-occurring vesicle-forming lipids, including the phospholipids, such as phosphatidylcholine (PC), phosphatidylethanolamine (PE), phosphatidylserine (PS), phosphatidic acid, phosphatidylinositol (PI), phosphatidylglycerol (PG), and sphingomyelin, where the two hydrocarbon chains are typically between about 14–22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols such as cholesterol.

Preferred diacyl-chain lipids for use in the present invention include diacyl glycerol, phosphatidyl ethanolamine (PE) and phosphatidylglycerol (PG). These lipids are preferred for use as the vesicle-forming lipid, the major liposome component, and for use in the derivatized lipid described below. All of these phospholipids and others are available from specialized suppliers of phospholipids (e.g., Avanti Polar Lipids, Inc., Alabaster, Ala.) as well as from general chemical suppliers, such as Sigma Chemical Co. (St. Louis, Mo.).

The aqueous film and bulk aqueous phase may be any suitable aqueous solution, such as a buffered saline solution (e.g., PBS). The bulk solution can be readily changed (taking care, of course, to keep the supported bilayer submerged at all times) by, e.g., flow-through rinsing with a solution having a different composition.

Figure 4:
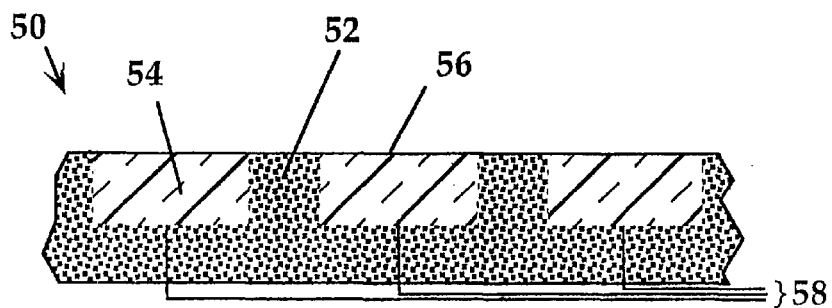
FIG. 4 shows the structural portion of a device of the invention suitable for use in a biosensor.

As described above, FIG. 1 shows a support grid microfabricated from a wafer of a material which forms the bilayer-compatible surfaces of the device. A device may also be microfabricated, however, from a wafer of a material which forms the bilayer-barrier surface regions of the device. One embodiment of such a device is shown in FIG. 4. Here, the structural portion 50 of a device of the invention is produced by microfabricating a wafer of a bilayer barrier material 52 (e.g., aluminum oxide) to contain regions, such as region 54, consisting of a bilayer-compatible material, where each region corresponds to one of the plurality of distinct bilayer-compatible surface regions, such as region 56. In one embodiment, the regions 54 are electrically-conductive and are connected to leads 58 which can be used to record changes in the membrane potential, membrane current, or capacitative transients. An example of an electrically-conductive bilayer-compatible material is a metal, such as gold, coated with a thin film of silicon oxide or polymer material to make the surface bilayer-compatible. The thin film of silicon oxide, while not an electrical conductor, can effectively pass capacitative current. Another suitable substrate is indium tin oxide (ITO) because of its conductivity and its ability to support direct membrane deposition (Sackmann & Tanaka, 2000; Hillebrandt, et al., 1999; Salafsky, J., Groves, J. T., and Boxer, 1996, each of which is herein incorporated by reference). Alternatively or in addition, electrodes having a bilayer-compatible surface may be generated from standard doped (e.g., boron-doped) silicon wafers. A layer of silicon oxide may be formed on such wafer substrates to provide a bilayer-compatible surface, under which resides a semi-conductor (doped silicon) electrode. The semi-conductor electrode can, of course, be interfaced with any of a variety of other elements, e.g., semi conductor elements in the substrate itself or in a separate chip, as desired, to facilitate or enhance the processing of information from the patch of bilayer membrane corresponding to that electrode.

A number of different devices have been produced in accordance with the invention. They include the following: (i) a device containing a 1 $cm^2$ array of 2500 identical 200 $\mu$m square corrals or regions, (ii) a device containing a 1 $cm^2$ array of 10,000 identical 100 $\mu$m square regions, (iii) a device containing a 1 $cm^2$ array of about 37,000 identical 50 $\mu$m square regions separated by 2 $\mu$m barriers of photoresist, and (iv) a device containing a 1 $cm^2$ array of about 2.8 million 5 $\mu$m square corrals or regions separated by 1 $\mu$m-wide barriers of photoresist.

Exemplary embodiments of the invention include devices where the bilayer lipid expanses contain different biomolecules, such as receptor protein molecules, ligand protein molecules, other protein molecules, or other integral membrane or membrane-associated biomolecules. Such devices are particularly useful in biosensors, described more fully in the applications section of the specification, and are made as described below by fusing proteoliposomes to the bilayer-compatible surface.

It is recognized that proteoliposome vesicles can be fused to a glass surface to create a planar supported membrane (Brian and McConnell, 1984). This technique has been successfully applied in a number of situations. In one example, the H-2K$^k$ protein was reconstituted into egg phosphatidylcholine-cholesterol vesicles by detergent dialysis, and the vesicles were used to create a planar membrane on glass (Brian and McConnell, 1984). The H-2K$^k$-containing membrane was capable of eliciting a specific cytotoxic response when brought into contact with a cell.

Chan, et al. (1991) demonstrated that a 5-glycosylphosphatidylinositol (GPI)-anchored membrane receptor is laterally mobile in planar membranes formed from proteoliposome fusion, and that this mobility enhances cell adhesion to the membrane. Other applications employ a combination of vesicle fusion, Langmuir-Blodgett methodology and derivatized surfaces to prepare supported membranes (Sui, et al., 1988; Plant, et al., 1995, both incorporated herein by reference).

In addition to incorporation of receptors or ion channels into the bilayer membrane, the bilayer may be derivatized with any of a number of groups or compounds to create a surface having the desired properties. For example, the liposomes may contain a ligand bound to the surface of the lipid by attachment to surface lipid components. Generally, such a ligand is coupled to the polar head group of a vesicle-forming lipid. Exemplary methods of achieving such coupling are described below.

III. Construction of a Surface Detector Device with Independently-Addressable Lipid Bilayer Regions Surface detector device of the invention may be conveniently produced using a combination of microfabrication and lipid vesicle technologies, e.g., as described in Example 1.

A. Microfabrication of Patterned Support Grid

Patterning of the substrate to produce a substrate surface having a plurality of distinct bilayer-compatible surface regions separated by one or more bilayer barrier regions may be done in a number of different ways appreciated by those knowledgeable in the microfabrication arts having the benefit of the present specification. For instance, micromachining methods well known in the art include film deposition processes, such as sputtering, spin coating and chemical vapor deposition, laser fabrication or photolithographic techniques, or etching methods, which may be performed by either wet chemical or plasma processes. These and other micromachining methods are summarized, for example, in Petersen (1982), incorporated herein by reference. General silicon processing techniques known in the art are described, for example, in Wolf and Tauber (1986) incorporated herein by reference.

A device is typically produced by first selecting a substrate material and producing a patterned support grid (the structural portion of a surface detector array device of the invention). The support grid carries on the patterned side the substrate surface according to the invention. The substrate is typically of a material selected to have the properties of one of either a bilayer-compatible or bilayer barrier material with strips of a material having the properties of the other of a bilayer-compatible or bilayer barrier material. In one general embodiment, a bilayer-compatible substrate material is patterned with strips of a bilayer-barrier material. In another general embodiment, the substrate material is a bilayer barrier material and its surface is patterned with regions of a bilayer-compatible material. It will be appreciated, however, that the substrate material can be patterned with both regions of bilayer-compatible material and regions of bilayer barrier material, such that the original substrate material is not represented at the patterned substrate surface. The materials which do form the substrate surface are selected such that after surface cleaning and/or treating, one yields a bilayer-compatible surface region and the other yields a bilayer barrier surface region.

Photoresist has at least two potential uses with respect to the present invention. As discussed above, positive photoresist is an effective bilayer-barrier material of course, photoresist can also be used in the traditional sense of patterning a substrate for subsequent lithography to generate microfabricated devices of the invention. Suitable negative- or positive-resist materials are well known. Common negative-resist materials include two-component bisarylazide/rubber resists, and positive-resist materials include two-component diazoquinone/phenolic resin materials. An example of electron beam resist, which may also be suitable, includes polymethylmethacrylate (PMMA) see, e.g., Thompson, et al. (1983).

As mentioned above, silicon is a preferred substrate material because of the well-developed technology permitting its precise and efficient fabrication, but other materials may be used, including polymers such as polytetrafluoroethylenes. The substrate wafer (e.g., silicon wafer) is typically cleaned using a standard RCA clean (Kern and Puotinen, 1970; Wolf and Tauber, 1986). The wafer is then oxidized at a temperature of between about 800 and 1000° C. in steam using known methods (Wolf and Tauber, 1986) until a layer of oxide (preferably about 0.5 $\mu$m in thickness) is formed. The oxide layer is then coated with a photoresist layer preferably about 1 $\mu$m in thickness. As described herein, this method can be used to produce the structural portion of an exemplary surface detector array device of the invention, which now only needs to be cleaned as described below before it is exposed to a vesicle suspension to generate the bilayer expanses. Alternatively, the photoresist-patterned substrate can be subjected to standard photolithography to produce a surface detector array device with a material other than photoresist forming the bilayer-barrier regions. In this case, the coated laminate is irradiated through a photomask imprinted with a pattern corresponding in size and layout to the desired pattern. Methods for forming photomasks having desired photomask patterns are well known. For example, quartz plates can be patterned with chrome with electron beam machine and an electron beam resist, such as PBS, using standard methods. Alternatively, a mask can be obtained commercially from any of a number of suppliers, e.g., Align-Rite (Burbank, Calif.). Exposure is carried out on a standard contact mask aligner machine, such as a Karl Suss contact lithography machine. Conventional positive or negative photoresists may be used with clear-field or dark-field photomasks. The pattern may be transferred to the substrate by subsequent etching or liftoff processes.

Electrodes may be fabricated into the device using any of a number of different techniques are available for applying thin metal coatings to a substrate in a desired pattern. These are reviewed in, for example, Krutenat, 1986; and in Wolf and Tauber, 1986, both incorporated herein by reference. Convenient and common techniques used in fabrication of microelectrodes include vacuum deposition, evaporation, sputtering, and plating. Various conductive materials, including doped silicon and metals such as platinum, gold, or silver may be used for the electrodes. Deposition techniques allowing precise control of the area of deposition are preferred for application of electrodes to the selected regions of the device. Such techniques are described, for example, in Krutenat, above, and in Wolf and Tauber. They include physical vapor deposition using an electron beam, where atoms are delivered on line-of-sight to the substrate from a virtual point source. In laser coating, a laser is focused onto the target point on the substrate, and a carrier gas projects powdered coating material into the beam, so that the molten particles are accelerated toward the substrate.

Another technique allowing precise targeting uses an electron beam to induce selective decomposition of a previously deposited substance, such as a conventional electron beam resist (e.g., PMMA), a thin layer of another material (e.g., a metal salt), a monolayer, or the like (see, e.g., Tiberio, et al., 1993). This technique has been used to produce sub-micron circuit paths (e.g., Ballantyne, et al., 1973). It will be appreciated that the dimensions of the different regions can be made extremely small, since electron beam lithography along with near field scanning microscopy may be used to generate and image membrane patterns on the nanometer scale. Further, certain nontraditional microfabrication materials having bilayer-barrier properties can be patterned using standard technologies. For example, aluminum oxide can be patterned on $SiO_2$ substrate wafers by evaporation and liftoff (Wolf and Tauber, 1986, see p. 535).

Such patterning, as well as the general microfabrication described above, can be conveniently done by contracting the work out to a company offering microfabrication services, such as MCNC (Research Triangle Park, N.C.), IC Sensors (Milpitas, Calif.) and Silica-Source Technology (Tempe, Ariz.).

B. Cleaning of Patterned Support Grid

After the patterned support grid is made, it is cleaned and/or treated to strip or etch off any impurities or contaminants present on the substrate surface which might otherwise inhibit the formation of a lipid bilayer adjacent the surface. The cleaning procedure is selected such that it does not substantially damage the functionality of the bilayer barrier regions. For example, embodiments where the barrier regions are made of photoresist should not be cleaned using the traditional piranha solution acid wash (3:1 $H_2SO_4:H_2O_2$), since the acid can strip off the bilayer barrier regions. An exemplary cleaning/treating process that does not damage the photoresist employs exposure of the patterned grid to argon or oxygen plasma for several minutes. Although the plasma does etch the photoresist somewhat, it strips off contaminants from the surface layer of the substrate (e.g., $SiO_2$ substrate) before substantially damaging the photoresist layer.

A number of suitable etching and/or cleaning procedures are known in the art. Four such procedures are summarized below. They include those described above and may be employed separately or in combination. In the first method, the structural portion of the device (support grid) is baked at 500° C. for several hours. This method is not compatible with gold or photoresist. In the second method, the support grid is washed in piranha solution acid wash (3:1 $H_2SO_4:H_2O_2$). This method is not compatible with photoresist and many metals, although it can be successfully used with gold and platinum. In the third method, the support grid is boiled in detergent (e g, 7× detergent from ICN Biomedicals, Inc. (Aurora, Ohio), diluted 1:4). This method is not compatible with photoresist and is not very effective used alone. In the fourth method, the support grid is etched in a gas plasma (e.g., argon or oxygen). This method works most effectively when combined with the third method, but can be used alone; it is the only procedure described herein that is suitable for use with photoresist.

C. Making Supported Bilayer Expanses

Following such a wash/etching/treatment step, the grid is placed in a chamber and a suspension of vesicles or liposomes formed of a selected lipid and (optionally) containing selected proteins or other biomolecules is contacted with each bilayer-compatible surface region. Vesicles in the suspension generally fuse with the bilayer-compatible surface region within minute or less to form a supported bilayer membrane (Xia, et al, 1996; Groves, et al, 1996). A humidified chamber is preferably used in applications where the volume of the drops of lipid suspension is small enough (e.g., ~<5 µl) to allow substantial evaporation before the bilayers form and the grid is flooded with bulk aqueous.

Liposomes may be prepared by a variety of techniques, such as those detailed in Szoka, Jr., et al. (1980). The lipid components used in forming liposomes useful in making the present invention preferably contain at least 70 percent vesicle-forming lipids. In one general embodiment, the bilayers are formed as described in Example 1.

As discussed above, the supported bilayers may contain receptors of other biomolecules, such as peptides, nucleic acids, factors, etc., attached to or incorporated into the supported bilayer membrane. Methods for producing such "modified" bilayers using "derivatized" liposomes, or liposomes containing an additional moiety such as a protein, are well known (see, e.g., Zalipsky, 1995; Allen, et al., 1995, as well as U.S. Pat. Nos. 6,605,630, 4,731,324, 4,429,008, 4,622,294 and 4,483,929). A few examples are discussed below.

One procedure suitable for preparation of such derivatized liposomes involves diffusion of polymer-lipid conjugates into preformed liposomes. In this method, liposomes are prepared from vesicle-forming lipids as described, and the preformed liposomes are added to a solution containing a concentrated dispersion of micelles of polymer-lipid conjugates. The mixture is then incubated under conditions effective to achieve insertion of the micellar lipids into the preformed liposomes.

In another method, the biomolecule is coupled to the lipid, by a coupling reaction described below, to form a biomolecule-lipid conjugate. This conjugate is added to a solution of lipids for formation of liposomes, as will be described. In another method, a vesicle-forming lipid activated for covalent attachment of a biomolecule is incorporated into liposomes. The formed liposomes are exposed to the biomolecule to achieve attachment of the biomolecule to the activated lipids. In yet another method, particularly suitable for making liposomes containing integral membrane receptors or proteins, the liposomes are simply formed in the presence of such proteins to make "proteoliposomes," as described below.

A variety of methods are available for preparing a conjugate composed of a biomolecule and a vesicle-forming lipid. For example, water-soluble, amine-containing biomolecules can be covalently attached to lipids, such as phosphatidylethanolamine, by reacting the amine-containing biomolecule with a lipid which has been derivatized to contain an activated ester of N-hydroxysuccinimide.

As another example, biomolecules, and in particular large biomolecules such as proteins, can be coupled to lipids according to reported methods. One method involves Schiff-base formation between an aldehyde group on a lipid, typically a phospholipid, and a primary amino acid on the biomolecule. The aldehyde group is preferably formed by periodate oxidation of the lipid. The coupling reaction, after removal of the oxidant, is carried out in the presence of a reducing agent, such as dithiothreitol, as described by Heath (1981). Typical aldehyde-lipid precursors suitable in the method include lactosylceramide, trihexosylceramine, galacto cerebroside, phosphatidylglycerol, phosphatidylinositol and gangliosides.

A second general coupling method is applicable to thiol-containing biomolecules, and involves formation of a disulfide or thioether bond between a lipid and the biomolecule. In the disulfide reaction, a lipid amine, such as phosphatidylethanolamine, is modified to contain a pyridyldithio derivative which can react with an exposed thiol group in the biomolecule. Reaction conditions for such a method can be found in Martin (1981). The thioether coupling method, described by Martin (1982), is carried out by forming a sulfhydryl-reactive phospholipid, such as N-(4)P-maleimidophenyl(butyryl)phosphatidylethanolamine, and reacting the lipid with the thiol-containing biomolecule.

Another method for reacting a biomolecule with a lipid involves reacting the biomolecule with a lipid which has been derivatized to contain an activated ester of N-hydroxysuccinimide. The reaction is typically carried out in the presence of a mild detergent, such as deoxycholate. Like the reactions described above, this coupling reaction is preferably performed prior to incorporating the lipid into the liposome. Methods for attachment of a biomolecule to the liposome through a short spacer arm have been described, such as in U.S. Pat. No. 4,762,915. In general, attachment of a moiety to a spacer arm can be accomplished by derivatizing the vesicle forming lipid, typically distearoyl phosphatidylethanolamine (DSPE), with a hydrophilic polymer, such as polyethylene glycol (PEG), having a reactive terminal group for attachment of an affinity moiety. Methods for attachment of ligands to activated PEG chains are described in the art (Allen, et al., 1995; Zalipsky, 1992a; Zalipsky, 1992b; Zalipsky, 1993; Zalipsky, 1994). In these methods, the inert terminal methoxy group of mPEG is replaced with a reactive functionality suitable for conjugation reactions, such as an amino or hydrazide group. The end functionalized PEG is attached to a lipid, typically DSPE.

The functionalized PEG-DSPE derivatives are employed in liposome formation and the desired ligand (i.e., biomolecule) is attached to the reactive end of the PEG chain before or after liposome formation.

Another method of linking biomolecules such as proteins to a supported lipid bilayer is via specific interactions between the side chain of the amino acid histidine and divalent transition metal ions (Malik, et al., 1994; Arnold, 1991) immobilized on the membrane surface. This method has been used, for example, to attach various proteins and peptides to lipid monolayers (Shnek, et al., 1994; Frey, et al., 1996; Sigal, et al., 1996). Briefly, a cDNA encoding the ligand or receptor which is immobilized to the bilayer surface is engineered so that the ligand or receptor contains a poly-histidine (e.g., hexahistidine) tag at one of its termini (e.g., the C-terminus). The bilayer is formed of or derivatized with metal-chelating moieties (e.g., copper-chelating moieties or lipids (Shnek, et al., 1994; Frey, et al., 1996)), and the expressed His-tagged protein is incubated with the vesicles used to generate the supported bilayer, or with the supported bilayer itself.

Specific high-affinity molecular interactions may also be employed to link selected biomolecules to a supported bilayer. For example, a bilayer expanse may be formed to include biotinylated lipids (available from, e.g., Molecular Probes, Eugene, Oreg.), and a biomolecule linked or coupled to avidin or streptavidin may be linked to the bilayer via the biotin moieties. Biomolecules may also be linked to a supported lipid bilayer via glycan-phosphatidyl inositol (GPI). The proteins to be linked can be genetically engineered to contain a GPI linkage (Caras, et al., 1987; Whitehorn, et al., 1995). Incorporation of a GPI attachment signal into a gene will cause the protein to be post-translationally modified by the cell resulting in a GPI linkage at the signal position. It will be appreciated that this type of alteration generally does not affect the molecular recognition properties of proteins such as the ones described here (Lin, et al., 1990; McHugh, et al., 1995; Wettstein, et al., 1991).

A convenient approach is to clone the cDNA sequence encoding the protein of interest into a vector containing the GPI attachment signal using standard molecular biology methods and procedures (see, e.g., Ausubel, et al., 1988; Sambrook, et al., 1989). An exemplary vector is the pBJ1Neo derivative described in Whitehorn, et al., (1995), which contains a modified polylinker and the human placental alkaline phosphatase (HPAP) GPI linkage signal. Another suitable vector is pBJ1Neo (Lin, et al., 1990). The construct is then transfected into suitable host cells (e.g., Chinese hamster ovary (CHO) cells) using a standard transfection method, such as electroporation (e.g., using settings of ~0.23 kV/960 $\mu$F). Transfected cells are selected, e.g., using fluorescence activated cell sorting (FACS) with an antibody directed against the protein of interest.

Transfected CHO cells with high surface expression are expanded in culture. GPI-linked proteins are purified from the cell membrane fraction by, e.g., detergent extraction (Schild, et al., 1994). Briefly, almost confluent CHO cells are washed free of medium with PBS containing a cocktail of proteinase and phosphatase inhibitors. The cells are lysed on ice in the same buffer containing 0.5% NP40. Nuclei and cell debris are spun out and the supernatant is loaded on an antibody affinity column.

The detergent is then exchanged to 1% Octylglucoside (OG) on the column, and the proteins are eluted by base (pH 11.5) containing 1% OG. After elution, the proteins are either stored in neutralized elution buffer or the buffer is exchanged with to OG in PBS. The purified GPI-linked proteins, or any other desired proteins or receptors, may then be incorporated into proteoliposomes as described below.

Proteoliposomes containing a selected membrane protein may be prepared using standard methods, e.g., using the protocol described by Sadler, et al. (1984). In this method, recombinant receptor proteins are concentrated in a suitable buffer (e.g., 10 mM Tris pH 8.0, 0.1% LDAO buffer) using, for example, a DEAE ion-exchange column or Centricon concentrator (Amicon Co., Beverly, Mass.). If desired, the salt concentration may be adjusted to a desired value (e.g., 100 mM NaCl) by dialysis.

The concentrated receptor proteins are then added to a suspension of small unilamellar vesicles (SUVs; prepared as described below; optionally with a lipid label such as Texas Red), e.g., in a small conical-bottom vial with stirring, to a selected final protein:lipid mole ratio. The ratio is generally between about 1:100 and 1:1000, preferably between about 1:300 and 1:500. In one embodiment, the ratio is 1:350.

In the case of the GPI-linked proteins described above, the proteins, at concentrations of around 100 nM, are mixed with SUVs, at a lipid concentration of 1 mM, in TN25/50, with the total OG concentration preferably not exceeding 0.15%. The detergent may removed by dialysis against three changes of 1 liter TN25/50 at 4° C. After dialysis, the lipid concentration may be determined using the NBD-PE absorption at 465 rum and adjusted to 0.2 mg/ml.

Alternatively, the samples may be run on a Sepharose column (e.g., a Sepharose CL-4B (Sigma) column), previously equilibrated with SUVs to minimize lipid adsorption, and fractions are collected. The absorption spectra of the proteoliposome fractions are measured, and the true protein:lipid mole ratio calculated using the absorption peak of the lipid label. Typically, the mole ratio of protein:lipid in the fractions follows a monotonic decrease, beginning at about 1:300 and ending at about 1:1000–1200. Only the fractions with a mole ratio of about 1:500 or lower are generally used to make planar supported bilayers; the fractions with higher mole ratios do not always form uniform planar bilayers.

IV. Applications

A. Biosensors

In one aspect, the invention includes a biosensor having a surface detection array device. The detection array device comprises (i) a substrate having a surface defining a plurality of distinct bilayer-compatible surface regions separated by one or more bilayer barrier regions, (ii) a bulk aqueous phase covering the substrate surface, (iii) a lipid bilayer expanse carried on each of the bilayer-compatible surface regions, and (iv) an aqueous film interposed between each bilayer-compatible surface region and corresponding lipid bilayer expanse, where each bilayer expanse contains a specie of receptor or biomolecule, and different bilayer expanses contain different species of receptors or biomolecules. The receptor or biomolecule is anchored to or in each lipid bilayer expanse. The specific binding of a particular ligand to a receptor in a lipid expanse is detected by any of a variety of known biosensor detection mechanisms, such as optical or electrical detection. In biosensors employing electrical detection, the support grid preferably contains a conductive electrode and electronic lead for each array element of the device. The leads typically terminate as extensions or "pins" from the device, which can be interfaced with a connector cable or ribbon leading to a processor. The electrodes preferably form at least a portion of the bilayer-compatible surface and are separated from one another by strips of insulating material. They can be used to detect capacitative transients as well as conductive currents (that may be sustained or transient). In one embodiment, the electrodes form a portion of the bilayer-compatible surface. In another embodiment, the construction of which is detailed in Example 5, the electrodes are positioned just beneath the bilayer-compatible surface, i.e., the electrode surface is coated with a thin layer of material, such as low-temperature grown oxide (e.g., $SiO_2$), which forms the bilayer-compatible surface. In embodiments where this layer is an insulating material, it is preferably less than about 1 μm in thickness to enable the detection of capacitative transients caused by binding of ligands to ionophoric receptors. One embodiment of the structural portion of a surface detection array device suitable for use with a biosensor is shown in FIG. 4, as described above.

The device is connected to or interfaced with a processor, which stores and/or analyzes the signal from each array element. The processor in turn forwards the data to computer memory (either hard disk or RAM) from where it can be used by a software program to further analyze, print and/or display the results.

Biosensors employing arrays of independently-addressable receptor-containing lipid bilayer regions have a number of advantages over previously-available biosensors. For example, the bilayer membrane fluidity endows devices of the invention with surface properties similar to those of living cells (e.g., Chan, et al., 1991; Tozeren, et al., 1992). In one particularly compelling set of studies, it was shown that purified major histocompatibility complex protein incorporated into a supported membrane can effectively replace the antigen presenting cell in the presentation of a reprocessed antigen to a helper T-cell (McConnell, et al., 1986; Watts and McConnell, 1987).

1. Detection Methods. Receptor-based biosensors operate by detecting the specific binding of selected analytes to "receptor" biomolecules on the biosensor. Since the present invention employs fluid bilayers resembling cell membranes, virtually any transmembrane, membrane-anchored or membrane-associated protein, carbohydrate, lipid, nucleic acid or other biomolecule can be used as the receptor. The receptor is incorporated into the lipid vesicles used to generate the bilayer expanses of the surface detector array devices. Binding of ligand to a receptor is typically detected either optically or electrically/electrochemically.

Optical detection methods include ellipsometry (Corsel, et al., 1986; Jönsson, et al., 1985; Vroman and Adams, 1969), optical wave guidance (Nellen and Lukosz, 1990) and surface plasmon resonance (SPR, Cullen, et al., 1988; Liedberg, et al., 1983). SPR is particular advantageous for monitoring molecular interactions in real-time, enabling a sensitive and comprehensive analysis of the degree of binding interactions between molecules.

In this approach, support grid is produced by making a support grid of an array of conductive regions (e.g., gold) separated by bilayer barrier regions. A very thin polymer film (e.g., polyacrylamide or dextran; Elender, et al., 1996; Khüner, et al., 1994) is then deposited on the conductive regions to form bilayer-compatible surface regions. Khüner, et al., (1994) describe the coupling of polyacrylamide to a surface by 3-methacryl-oxypropyl-trimethoxy-silane (MPTS; Serva, Heidelberg, Germany).

Bilayers containing the selected molecules are deposited as described, and the bilayer-containing support grid is placed into a cell which allows a solution to be passed over the surface containing the array of receptor-studded lipid expanses. The grid is illuminated at an angle with a light-emitting diode (LED), and reflected light is analyzed with a photodetector. Through an evanescent electric field generated by the interaction of incident light with the gold layer, the reflected light is sensitive to the environment of a layer extending about 1 μm ($\lambda$=760 nm) from the receptors into the medium. Changes in the environment of the receptor, such as are caused by the binding of a ligand to the receptor, are detected as changes in the reflectance intensity at a specific angle of reflection (the resonance angle).

Capacitative detection or impedance analysis may also be used. Here, an electrode is incorporated into each the bilayer-compatible surface region, and a "ground" electrode is placed in the bulk aqueous phase. A voltage from a variable-frequency function generator is used to generate a selected voltage waveform which is fed across selected array elements. The peak-to-peak amplitude of the voltage is typically on the order of about 10 V, but can be substantially less. The voltage is applied over a range of frequencies and the capacitance is determined from the measured current as a function of signal frequency using standard signal-processing techniques. Examples of the application of capacitance measurements and impedance analyses of supported bilayers are discussed, for example, in Stelzle, et al., (1993) and Stelzle and Sackmann (1989), both incorporated herein by reference.

Other methods of detection are discussed in U.S. Patents relating to biosensors, including Gitler, et al., 1993; Osman, et al., 1993; Taylor, et al., 1993; Case, et al., 1994; and Tomich, et al., 1994, all incorporated herein by reference.

2. Making of Biosensors. A surface detection array device is produced essentially as described above, except that (i) the vesicles used to make the bilayer expanse typically contain the desired receptor or biomolecule (although the receptor or biomolecule may also be introduced after the bilayer is formed), and (ii) different array elements are typically made with different vesicle suspensions.

Analyte selectivity is conferred to different array elements by different types of receptors present in the supported bilayer of each array element. Such distinct bilayer may be formed using liposomes or proteoliposomes containing the different biomolecules or receptors. A convenient method of making such a device is by depositing micro-droplets of the desired liposome suspension in the different compartments of a device substrate housed in a humidified chamber to eliminate fluid loss due to evaporation.

Any of several approaches known in the art can be used to form different-composition bilayers on a single microfabricated support grid. One suitable method employs a modified ink-jet printing device (Blanchard, et al., 1996, incorporated herein by reference) to deposit micro-drops containing selected vesicle suspensions on the individual bilayer-compatible surface regions of the device in a humidified chamber. The ink-jet print head of the device is modified to deliver small drops (e.g., ~100 $\mu$m in diameter) of vesicle-containing suspension in a high density array format. Adjacent drops may be deposited as close as 30 $\mu$m from one another. The barriers in such applications have a width that is typically on the order of the minimum separation distance between adjacent drops (i.e., ~30 $\mu$m), but can be greater or smaller in particular applications.

Of course, the vesicle suspensions may also be deposited using standard micropipeting technology (i.e., a micropipet in a holder connected to a micromanipulator). The micromanipulator may be controlled by a motorized drive for greater precision and efficiency. Such drives, as well as micromanipulators, are commercially available, e.g., from Newport Corp., (Irvine, Calif.) and Narashige USA, Inc. (Greenvale, N.Y.). The drive in turn can be controlled by a microcomputer for fully automated operation. The entire process can be monitored, if desired, using a conventional microscope, such as a dissecting microscope. Suitable micropipettes may be made using a standard micropipet puller, such as a puller available from Narashige.

The tips of the pipets can be made to have opening diameters ranging from less than a micron to hundreds of microns or more. The back of the pipet can be connected to a standard microinjection pump set to dispense a desired volume of vesicle suspension.

The drops containing the vesicle suspensions are allowed to incubate on the substrate grid for a few minutes to allow essentially all the membranes that are capable of forming to form. The grid is then gently flooded with aqueous solution until a suitable bulk aqueous phase is established above the bilayer membranes. A convenient method of flooding the grid without significantly disturbing the bilayers is to bring the level of aqueous in the chamber up until the surface is flush with the top of the grid, but the compartments still contain only the originally-deposited drops. The top of the grid is then exposed to a fine mist of the aqueous solution until the droplets coalesce into a uniform film of aqueous solution. The level of solution is then raised to achieve a desired volume of bulk phase aqueous above the grid.

3. Use of Biosensors. A biosensor employing a biosensor surface detector array device such as described above can be used to detect low concentrations of biologically-active analytes or ligands in a solution containing a complex mixture of ligands. In such a method, the surface detector array device is constructed with different receptors in the bilayer expanses at different array positions. To control for signal fluctuations, several different array elements may contain the same type of receptor. Similarly, designated array elements may be used for positive and/or negative control purposes.

The biosensor surface detector array device is then contacted with an aqueous solution containing a mixture of ligands to be analyzed for the presence of selected ligands, such as receptor agonists, where the contacting takes place via the bulk aqueous solution portion of the device. In other words, the mixture to be tested is washed over the device, replacing the bulk aqueous portion. When a selected ligand specifically binds to a receptor, the binding is detected by a suitable detection method. For example, in an assay for the presence of acetylcholine (Ach) using an array device containing Ach receptors (AchRs) incorporated into the lipid expanse of at least one array element, the binding of Ach to the AchRs is detected as a change in the transmembrane voltage or current in the element containing the AchRs.

B. Substrate for Bioactivity Screens

In an embodiment related to the biosensor application described above, devices of the present invention may be used as substrates for holding an array of receptors employed in bioactivity screens of compounds. In particular, high-throughput screens of large libraries of compounds are typically optimized for speed and efficiency in order to rapidly identify candidate compounds for subsequent bioactivity testing. When such bioactivity testing involves, for example, assays for ion channel agonists or antagonist activity, the testing is often done one compound at a time by a scientist using electrophysiological measurements (e.g., patch clamping; see, e.g., Hamill, et al., 1981) of individual cells expressing the target ion channel or receptor. While this type of analysis provides detailed high quality data for each compound, it is slow and inefficient if a large number of compounds are to be assayed for bioactivity. Devices of the invention may be used in secondary screen to assess the bioactivity of compounds identified in a high-throughput screen, enabling the scientists to focus on the few truly-interesting compounds. The devices are made essentially as described above for biosensors. The same types of binding-detection schemes may be employed, although when assaying compounds for bioactivity on ionotrophic receptors or ion channels, electrical detection is typically preferred to optical detection.

In devices employing electrical detection using electrodes in each of the array elements, it will be appreciated that since a water film separates the electrode from the bilayer, an electric field may be applied across the bilayer membrane, e.g., to activate voltage-dependent ion channels. This allows screening for compounds that only bind to the channel when the channel is in a state other than the native resting state (e.g., in an activated or inactivated state).

In a related embodiment, devices of the invention are used as substrates for holding libraries of compounds (e.g., combinatorial small molecule libraries, combinatorial biological libraries such as combinatorial peptide or nucleic acid libraries, or any other type of random or non-random group of compounds that may be employed using the methods of the present invention). The bilayer expanses are deposited onto a support grid from a common bulk vesicle suspension, as detailed in Example 1, and each bilayer expanse region is then derivatized with a selected biomolecule, e.g., using one of the methods detailed above one application if this approach is the use of light-directed synthesis (Fodor, et al., 1991) to generate spatially-addressable molecular libraries (e.g., peptide libraries) in a form where the peptides are displayed on the surface of the confined patches of fluid membrane. This is somewhat analogous to phage display, except that here the peptide sequence is defined by its location in the array. Such libraries may be particularly useful for cell screening due to the native-like surface provided by the membrane.

C. Forming Regions with a High Density of Membrane Proteins

The invention also includes a method of forming supported bilayers with regions of very high membrane protein density. As stated above, protein-containing vesicles, or proteoliposomes, can typically only be formed with a protein:lipid mole ratio of about 1:500 or lower; vesicles with higher mole ratios do not consistently form uniform planar bilayers. Accordingly, high-density arrays of proteins in lipid bilayers cannot be formed by simply fusing protein-containing vesicles with a surface to form a supported bilayer.

Figure 3:
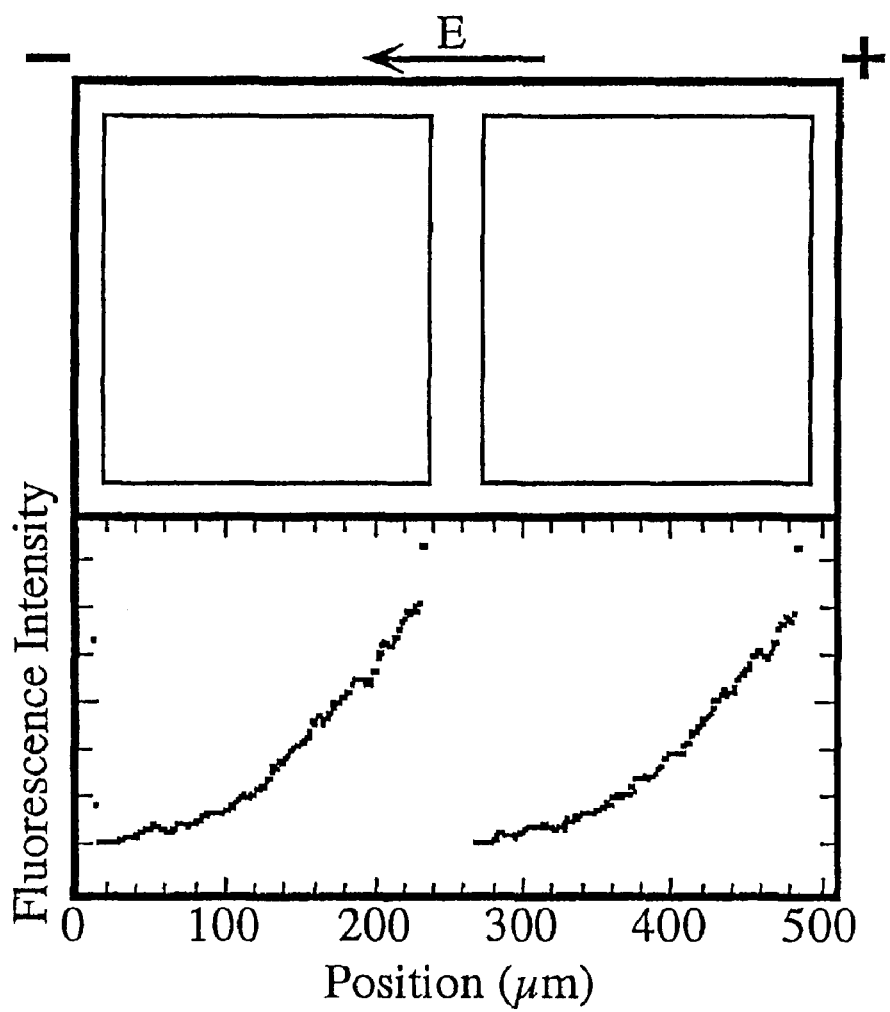
FIG. 3 shows the fluorescence intensity from two regions of a surface detector array device, each containing a field-induced concentration gradient of charged fluorescent reporter lipids.

As shown in Example 3 and FIG. 3, however, if the supported bilayer is formed in a corral surrounded by bilayer barrier regions and subjected to an electric field, the membrane proteins can be concentrated into regions of very high density. This effect can be amplified by, for example, making the migration focal point the apex of a triangular corral.

After the proteins have been concentrated, they can be used for subsequent applications, such as diffraction studies to determine structure. If desired, the high-density protein region of the field-induced concentration gradient can be "frozen" by cross-linking the proteins using standard cross-linking methods (e.g., treatment with glutaraldehyde).

D. Device for Measuring Receptor Size and/or Aggregation

Figure 5:
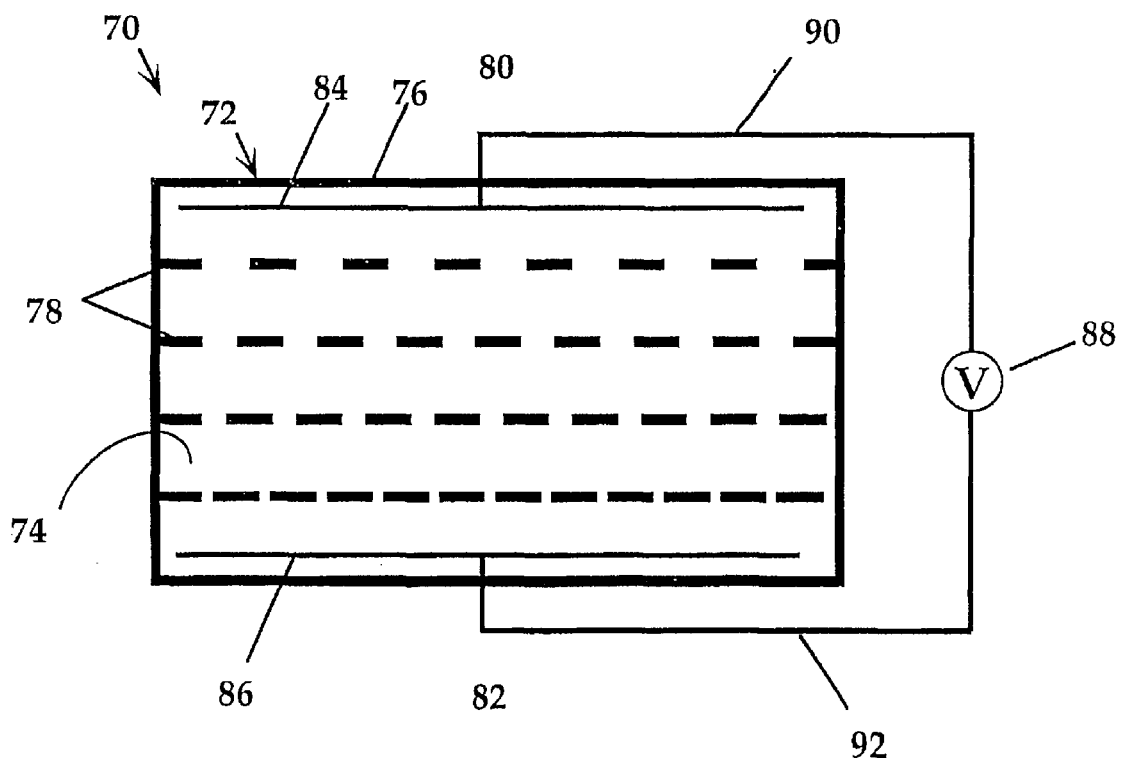
FIG. 5 shows the structural portion of a device of the invention suitable for use in separating membrane-associated molecules by size.

Another aspect of the invention relates to sorting devices for biomolecules integrated into or attached to the supported bilayer. The sorting devices employ the bilayer barrier surface regions not to compartmentalize the surface into discrete patches, but rather, to act as 2-dimensional sieves having progressively smaller "openings" from one end of the device to the other. One embodiment of the structural portion of this aspect of the invention is shown in a top view in FIG. 5. Here, the structural portion of the device 70 is formed of a wafer 72 having a substrate surface 74 defining a bilayer-compatible region bounded on all sides by a bilayer barrier region 76. The bilayer-compatible region is also interrupted by a plurality of substantially parallel broken lines 78 defining bilayer barrier surface regions. The gaps in the lines are of molecular dimensions and get progressively smaller going from one edge 80 of the device to the opposite edge 82. Electrodes 84, 86 are positioned near the edges of the device and are connected to a voltage source 88 via wires 90, 92.

The device is employed to sort membrane-associated molecules by size. A mixture of like-charged molecules having different sizes is loaded in the well formed by the bilayer barrier region circumscribing and the broken line having the largest gaps. The voltage source is turned on with a polarity to cause the charged biomolecules to migrate through the progressively smaller gaps of the consecutive barriers until they get trapped according to size in the well defined on the "downstream" side by a barrier having gaps too small for the molecules to pass through.

In a related application, the bilayer barrier regions are arranged to provide a uniform or graded array or network of barriers, and electrophoresed membrane molecules are sorted based on the migration time through the array. Here, the method of separation is similar to that obtained with a gel, such as an agarose or polyacrylamide gel, where smaller molecules migrate faster than larger molecules.

In another aspect of the invention, the biosensor array further comprises a plurality of biosensors where one or more biosensors in the array has a bilayer composition different than the remaining other biosensors present within the biosensor array. The resulting gradient biosensor array forms at least a one-dimensional or two-dimensional gradient across it with respect to the local concentration of bilayer composition upon each biosensor. Although at the initial formation of the gradient, a sub-gradient may exist across any one particular biosensor, such sub-gradient rapidly homogenizes within the confines of the lipid bilayer region captured by a particular bilayer-compatible region situated under each bilayer.

As discussed above, when lipid-bilayer-forming compositions containing lipid vesicles are contacted with a bilayer-compatible region that is surrounded by one or more bilayer-barrier regions, the vesicles fuse at each bilayer-compatible region surface to form a continuous bilayer expanse thereabove. Because each bilayer expanse is separated from the other by the presence of the bilayer-barrier regions, the resulting bilayer expanses supported above each region are in two-dimensional matrix isolation from one another. Consequently, the compositions of different, yet adjacent bilayer expanses above bilayer-compatible regions will remain distinct despite their close proximity. Such result provides the unexpected advantage of allowing a user to rapidly and reliable create a biosensor array having a plurality of different biosensor regions, each region having a distinctly different bilayer composition for its adjacent bilayer expanse. Bilayer composition means, for the purpose of this section, both the chemical components of the bilayer itself, and any other components that are lipid-deliverable during delivery as lipid-bilayer forming vesicles, for example, receptor subunits, different receptors, other cell membrane communication factors, and the like. Differing ratios of receptor subunits may be "titered" out using this method. Additionally, the method can be used to create different ratios of bilayer forming components, for example different phospholipids.

A gradient biosensor array may be created by contacting different bilayer compositions with different bilayer-compatible region within a biosensor array such that each different composition remains within its respective bilayer-compatible region and is separated from other, different bilayer composition containing bilayer-compatible regions by one or more bilayer-incompatible regions. One method includes selectively contacting different bilayer-forming compositions with different areas of a biosensor array that each contain a plurality of bilayer-compatible regions separated from one another by one or more bilayer-barrier regions resulting in a biosensor array with a plurality of different areas each containing a plurality of bilayer-compatible regions having the same composition within such area, but different from other areas within the biosensor array.

Gradients can be formed in a variety of ways. For example, a simple two-dimensional gradient can be formed by drawing a mixture from at least two containers in fluid communication with one another through a small diameter bore channel such as a capillary tube. In its simplest form, two bottles placed side by side, may be connected by a small bore siphon tube, and fluid removed from the one of the two bottles of the two bottle system by yet another tube via pumping or siphonic action. Each bottle contains a different concentration of the component that will form the gradient. Depending on which bottle is drawn from, either the high concentration or low concentration, a high to low, or a low to high effluent gradient is formed as the twobottle system is drawn upon. The effluent may then be further passed through a wide spreading—thin profile nozzle to coat a surface of a biosensor array. By moving the array laterally with respect to the nozzle, a gradient of mixtures across the biosensor surface is formed. Gradient forming devices are known in the art, for example, as found in U.S. Pat. Nos. 3,840,040, 4,074,6878, and 4,966,792, each included entirely by reference herein, which may be further adapted in accordance with the present invention to yield a device for forming a gradient biosensor array.

Yet another aspect of the invention provides for a method for forming an array of biosensor regions, where each region has a different, known lipid bilayer compositions comprising the steps of providing a biosensor array having a plurality of lipid bilayer compatible regions, each compatible region being surrounded by one or more bilayer barrier regions, providing a gradient forming devices loaded with two or more different lipid bilayer compositions, the gradient forming device in fluid communication with a spot forming device for forming spots on a surface, providing a multi-axis translation table for holding and translating a biosensor array workpiece, and placing a biosensor array workpiece that has a plurality of bilayer compatible regions surrounded by one or more barrier regions, and forming spots of mixed lipid bilayer compositions resulting from the gradient forming device forming a gradient and translating the table in at least one axis while dispensing such composition mixture as it is formed thereby dispensing to different, consecutive locations different ratios of each lipid bilayer compositions. Thus, as a gradient of lipid bilayer compositions is formed with respect to the ratio of each composition, the result of such gradient is distributed across the array of biosensors by raster scanning the relative position of the spot forming device's output across the surface of the array and thereby depositing at different-biosensor locations, different composition mixtures.

In yet another embodiment of the invention, a gradient may be formed across a surface of an array of biosensors in one dimension. This method for making a gradient biosensor array comprises the steps of: mixing together first and second different lipid bilayer forming compositions contained from first and second sources by flowing in a substantially laminar flow, two different compositions from two different sources into one mixing chamber that substantially retains the laminar flow character of the two different compositions while flowing through the mixing chamber, where the facing edges of each different composition mix to form a gradient having a first edge and a second edge and further comprising composition combinations of different ratios beginning from the first edge of the gradient that faces the first composition, and ending at the second edge of the gradient that faces the other, second composition, and where the mixing chamber is adapted to dispense the gradient in a substantially laminar flow across the surface of the array, and where the compositions contained in the gradient are captured and retained upon initial contact by bilayer-compatible regions of the array. Other embodiments may further comprise the mixing chamber being the surface of the biosensor array where the first and second compositions are supplied to the surface by a plurality of sources adjacent to the array, each containing a different composition. Further, other embodiments may further comprise a plurality of different compositions contained within a plurality of different sources in fluid communication with the mixing chamber.

In accordance with the present invention, lipid bilayers spontaneously form over lipid bilayer regions distributed across the array. For example, as a gradient mixture is dispensed from a gradient forming device, and such mixture contacts a biosensor array containing a plurality of bilayer-compatible regions surrounded by one or more bilayer-barrier regions, components of the mixture, such as lipid bilayer vesicles optionally containing other bilayer components, contact the bilayer-compatible regions and spontaneously form continuous lipid bilayers adjacent to each bilayer-compatible region, but with each such continuous bilayer being discontinuous from other continuous bilayer regions, separated from one another by bilayer-incompatible regions. The attractive, bilayer forming forces associated with each bilayer-compatible region serve to capture from the gradient mixture the instant mixture initially present to the bilayer-compatible region thus forming and retaining the mixture character of the gradient mixture initially presented to such bilayer-compatible region despite subsequent presentation of gradient mixtures different than what was initially presented to the bilayer-compatible region during the formation of the gradient biosensor array. Once a lipid-bilayer region is formed, its composition, in general, is not susceptible to change if exposed to lipid bilayer forming compositions.

In still yet another embodiment of the invention, a plurality of gradient forming devices are in fluid communication with one or more secondary gradient forming devices where a first gradient is combined with one or more different gradients to form a complex gradient forming device in fluid communication with a distribution devices for distributing a gradient mixture across an array of biosensors.

Figure 6A:
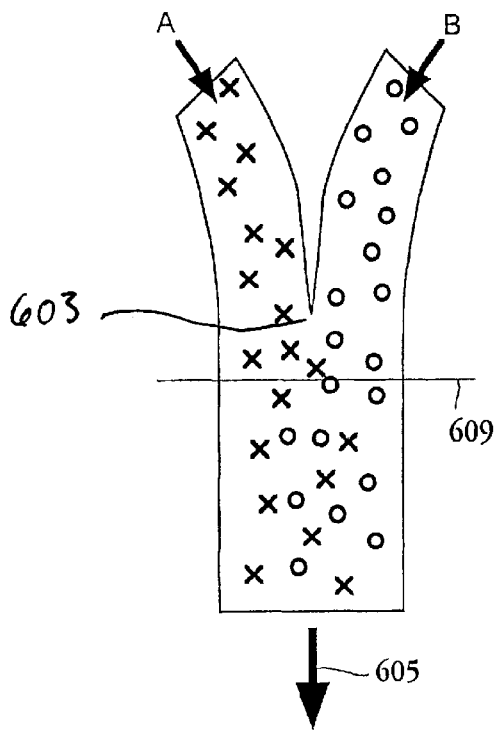
FIG. 6 depicts a top-down view of the forming of a gradient biosensor array.
Figure 6B:
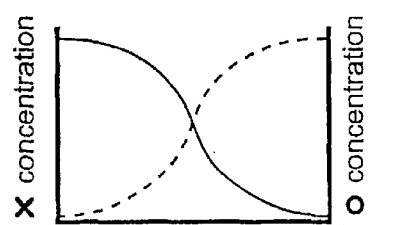
Figure 6C:
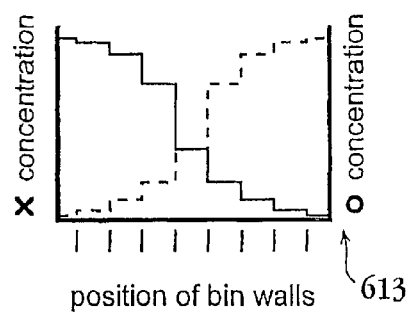

FIG. 6 depicts a top-down view of the forming of a gradient biosensor array. Lipid bilayer forming composition A combines with lipid bilayer forming composition B at point 603 in mixing device 605 to form a substantially laminar flow gradient flowing in direction 607. At a certain point, indicated by line 609 pointing to graph 611, the cross sectional profile of the mixture flow or effluent may be characterized by graph 611 showing the cross sectional concentration of both A and B at each point across the cross section. Graph 613 represents the bilayer composition at each distinct bilayer-compatible region within the gradient biosensor array.

Figure 7A:
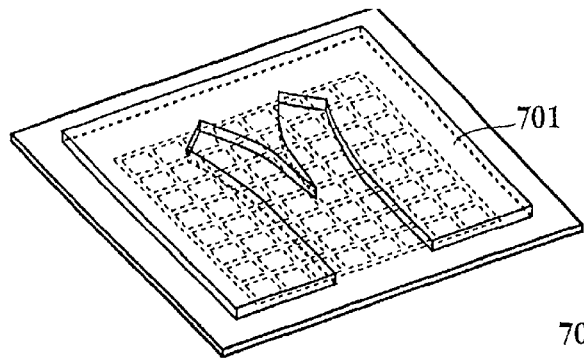
FIGS. 7a–d depict in color the formation of a two composition gradient biosensor array.
Figure 7B:
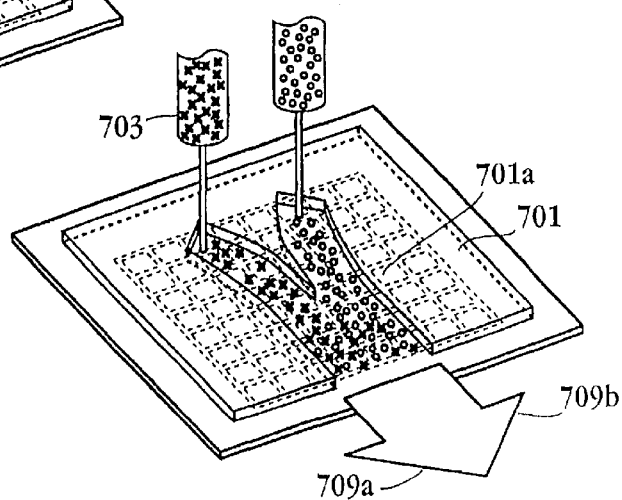
Figure 7C:
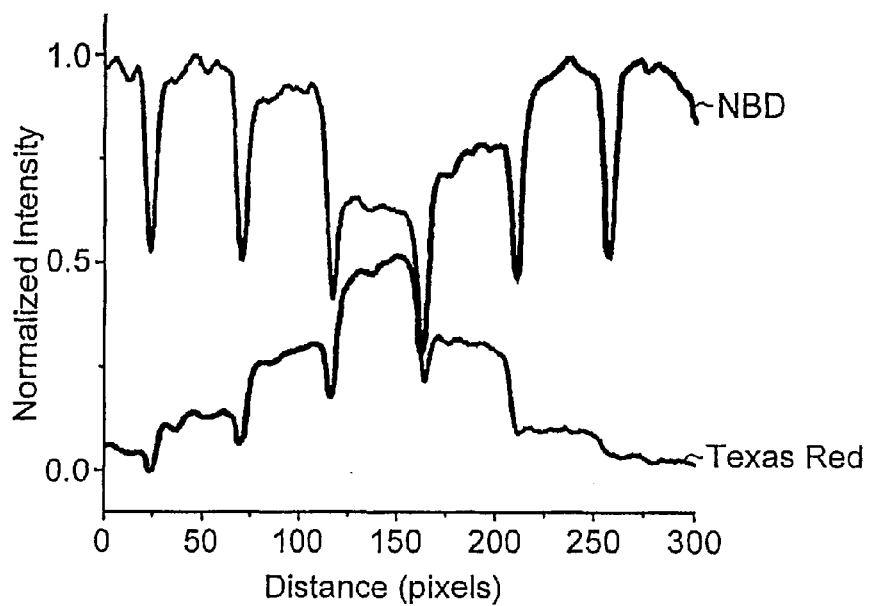
Figure 7D:
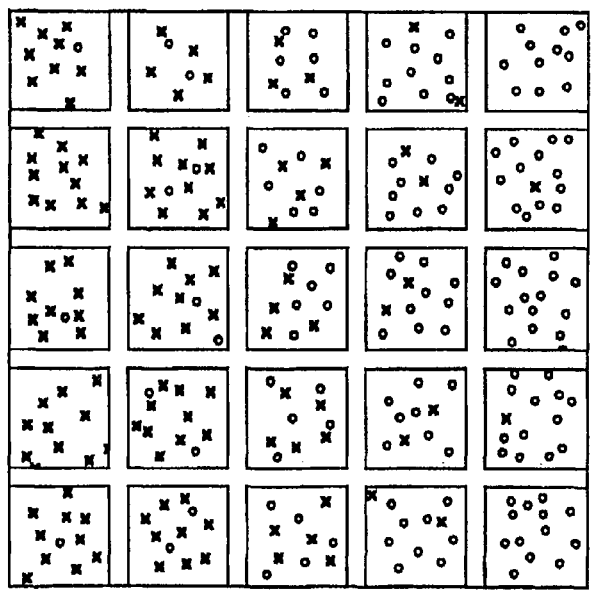

FIGS. 7*a*–*d* depict, in color, the formation of a two composition gradient biosensor array. In FIG. 7*a*, biosensor array 701 is slightly biased upward on one end with respect to gravity. In FIG. 7*b*, first bilayer forming component 703, TEXAS RED, is flowed onto array 701's surface 701*a*, while second bilayer forming component 705, NBD in green, is flowed onto surface 701*a*. The resulting flow streams from each component form a laninar flow across array 701 as indicated by arrows 709*a* and 709*b*. The resulting grid in FIG. 7*d* is graphically portrayed in FIG. 7*c* from data collected from spectral intensity analysis of the array in one dimension.

The following examples illustrate but in no way are intended to limit the present invention.

MATERIALS AND METHODS

Unless otherwise indicated, chemicals were purchased from Sigma (St. Louis, Mo.) or United States Biochemical (Cleveland, Ohio).

A. Buffers

Standard Buffer
  10 mM Tris
  100 mM NaCl (pH 8.0)
Phosphate-buffered saline (PBS)
  10×stock solution, 1 liter:
  80 g NaCl 2 g KCl
11.5 g Na$_2$HPO$_4$.7H$_2$O
2 g KH$_2$PO$_4$
Working solution of PBS, pH 7.3:
137 mM NaCl
2.7 MM KCl
4.3 mM Na$_2$HPO$_4$.7H$_2$O
1.4 mM KH$_2$PO$_4$

B. Lipids and Labels

L-α phosphatidylcholine from egg (egg-PC) were obtained from Avanti Polar Lipids (Alabaster, Ala.). The fluorescent probe N (Texas Red sulfonyl)-1,2-dihexadecanoyl-sn-glycero-3phosphoethanolamine, triethylammonium salt (Texas Red DHPE) was obtained from Molecular Probes (Eugene, Oreg.).

C. Preparation of Phospholipid Vesicles

Small unilamellar vesicles (SUVs) were prepared by following the protocol outlined in Barenholz, et al. (1977) using egg L-α phosphatidylcholine (Avanti). The phosphatidylcholine was mixed with 1 mole % Texas red DHPE in HPLC-grade chloroform (SigmaAldrich) and dried in a vacuum desiccator overnight. The dried lipids were resuspended to about 6 mg/ml in standard buffer which had been filtered through Rainin Nylon-66 0.45 μm filters using a Sibata filter unit. The suspension was sonicated to clarity with a Branson ultrasonicator under flowing Ar on ice for 3 minute periods separated by 1 minute cooling periods (Martin, 1990).

The sample was then spun for 30 minutes at 100,000×g to remove Ti particles shed from the sonicator tip, and the supernatant was spun for 4 hours at 166,000×g to obtain the SUVs. The SUVs were stored at 4° C. under N$_2$ or Ar in the dark and were used within three weeks. The lipid concentration in these samples was determined from the Texas Red probe absorption at 590 nm ($\epsilon$=100,000 M$^{-1}$cm$^{-1}$; Haugland, 1992) assuming that the probe concentration in the vesicles is 1 mole % as prepared. Yields (mg SUV lipid/mg initial lipid) are calculated from this concentration and are equal to those reported by Barenholz, et al. (1977).

D. Membrane Electrophoresis

For the electrophoretic studies, the supported membrane in PBS was diluted to 1 mM total ionic strength. This was then assembled, under buffer, into a sandwich with another coverslip. The electrophoresis cell consisted of two 0.01" diameter platinum wire electrodes in solution-filled wells of a Teflon trough. The coverslip sandwich was arranged to form a bridge between the two electrode wells. Electrical connection was achieved through the solution in the cover slip sandwich. Fields up to 60 V/cm were applied with a standard power supply. Currents were monitored with a Keithley picoammeter (Cleveland, Ohio) and were typically around 3 μA for a single 18 mm square coverslip sandwich at 15 V/cm. This corresponds to a total power dissipation of 9×10$^{-5}$ W which should produce a negligible amount of Joule heating.

EXAMPLE 1

Construction of a Surface Detector Device

A patterned support grid was microfabricated using standard techniques (Wolf and Tauber, 1986). 100 mm diameter silicon 1-0-0 wafers were obtained from Silrec Corporation (San Jose, Calif.). The wafers were maintained in steam at 1000° C. in an oxidation furnace (Tylan Inc., San Diego, Calif.) to generate a ~1 μm thick layer of thermal oxide. Standard positive photoresist (S1800; Shipley Inc., Marlborough, Mass.) was spun onto the wafers at a thickness of one micron with a track coater (Silicon Valley Group, San Jose, Calif.).

The wafers were exposed for 8 seconds to ~10 mW/cm$^2$ UV light through a photolithographic mask with a contact mask aligner (Karl Suss America (Waterbury Center, Vt.), MA-4). Development was done on a track developer (SVG) using standard tetramethylammonium hydroxide (TMAH)-based developer (Shipley). The wafers were then subjected to a three minute etch in argon plasma.

Membranes were formed by contacting the patterned surface of the wafer support grids with a suspension, prepared as described above, containing ~25 nm diameter unilamellar vesicles consisting primarily of L-α-phosphatidylcholine (PC) molecules doped with 1 mole percent of the fluorescently labeled lipid, Texas Red DHPE. Vesicles in the suspension spontaneously assembled in a matter of seconds to form a continuous single bilayer on the bilayer-compatible regions of the support grid, as evidenced by photobleaching and electrophoresis experiments described below. Excess vesicles were rinsed away while maintaining the membrane under the bulk aqueous solution at all times. Results of extended experiments monitoring the state of the supported bilayers indicated that the bilayers are stable under water and retain their uniformity and fluidity for a period of weeks.

EXAMPLE 2

Fluidity of Supported Bilayers Assayed by Photobleaching

Figure 2A:
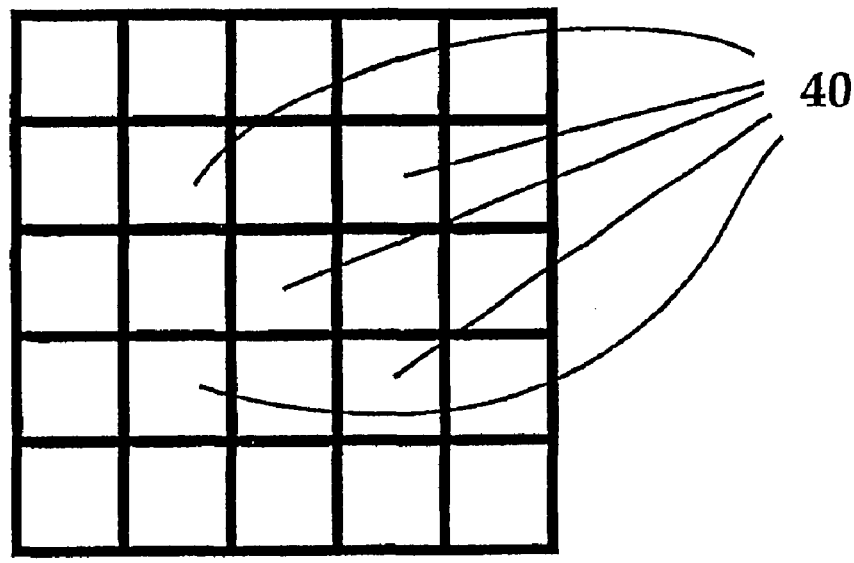
FIGS. 2A and 2B are schematics illustrating the effect of photobleaching fluorescent reporter lipids in the lipid bilayers of five distinct regions of a surface detector array device of the invention.

Long-range fluidity within the bilayer-compatible regions, or corrals, was observed by fluorescence recovery after photobleaching (FRAP). The experiment is described with respect to FIGS. 2A and 2B, which show schematics of a surface detector array device containing 25 bilayer-compatible surface regions, or corrals, with a corresponding lipid bilayer expanse carried on each of these surface regions. The device was made from an oxidized silicon wafer patterned with photoresist to generate corrals dimensioned 100 μm per side. The 10 μm wide photoresist (bilayer barrier regions) appears as the black boundaries separating the 25 corrals in FIGS. 2A and 2B. Texas Red DHPE lipid probe (Molecular Probes, Eugene, Oreg.) was incorporated in the bilayer membrane to serve as a label.

Figure 2B:
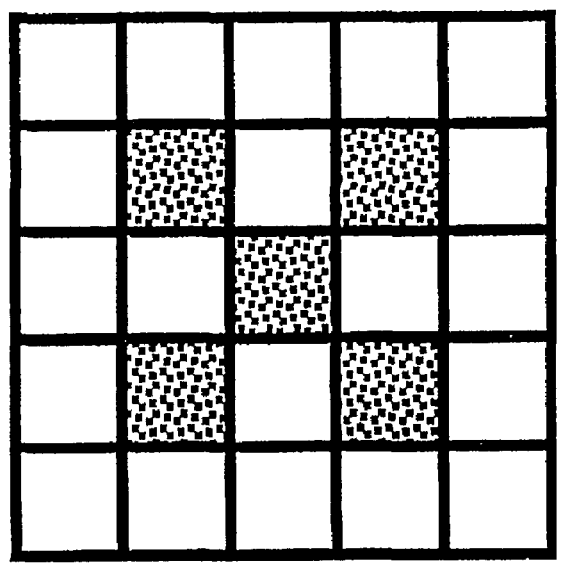

A circular beam of light having a diameter of less than 100 μm was used to photobleach the fluorescent probe molecules in five individual corrals 40 (FIG. 2A), yielding the results schematized in FIG. 2B. Diffusive mixing of molecules within each corral caused the circular bleached spot to spread, filling the square corral. The lines of photoresist acted as barriers to lateral diffusion, preventing mixing between separate corrals. Fluidity of the membrane was evidenced by the spreading of the bleached region to fill each square corral. If the membrane had not been fluid, a circular bleached (dark) region would have remained.

Bleach patterns such as those illustrated in FIG. 2B were stable for many days, whereas spots photobleached into a single continuous membrane with no such barriers diffused away completely in about 30 minutes.

EXAMPLE 3

Fluidity of Supported Bilayers Assayed by Electrophoresis

The fluidity of the supported bilayers on the bilayer-compatible surface regions was also assessed by electrophoretic redistribution of charged membrane components. This method illustrates both the fluidity of the lipid bilayer and confinement of different-composition bilayer patches to distinct independently-addressable bilayer-compatible surface regions.

A device with 200 μm square corrals was prepared as described above using PC molecules doped with 1 mole percent of the fluorescently labeled lipid, Texas Red DHPE (Molecular Probes).

An electric field of 15 V/cm was applied parallel to the lipid bilayer membrane. Upon application of the field, the charged molecules (labeled DHPE) drifted in the plane of the bilayer, whereas the neutral PC molecules, forming the bulk of the membrane, were unaffected by the field. Application of the field for ~25 minutes resulted in a steady-state, electric field-induced concentration profile (Groves and Boxer, 1995) of the negatively-charged fluorescent probe.

A quantitative description of the field-induced concentration gradient is depicted in FIG. 3, which shows quantitative traces of fluorescence intensity calculated from videomicrographs of steady-state concentration gradients of the fluorescent probe lipid (Texas Red DHPE) in two 200 μm microfabricated corrals. The concentration gradients in this experiment adopted an exponential profile. The image from which the fluorescence intensity traces were calculated was taken with a low light level video camera which had been adjusted for linear imaging of fluorescence intensity.

The field-induced concentration gradients were-fully reversible, taking approximately the same amount of time to dissipate as they took to form at 15 V/cm. The profiles could be switched by reversing the polarity of the field repeatedly without any apparent effect on the membrane or the bilayer-barrier regions, or barriers. The field-induced concentration profiles described above can be used to study molecular size, clustering, and non-ideal mixing.

EXAMPLE 4

Bilayer Barrier Regions Do Not Function by Mechanically Separating Adjacent Bilayer Expanses Experiments were performed to determine whether the bilayer barrier regions isolate adjacent bilayer expanses by mechanical separation or by intrinsic properties of the material making up the bilayer barrier surface regions. Bilayer membranes were deposited on unpatterned $SiO_2$ substrates (i.e., a substrate having a single bilayer-compatible surface) as described above. However, the topography of the bilayer-compatible surface was the same as that of the photoresist-patterned $SiO_2$ substrate described above.

Continuity of the bilayer(s) was assayed using the FRAP and electrophoretic methods described above. The results indicated that the lipid expanse was a single supported membrane which followed the contours of the corrugated surface without disruption.

EXAMPLE 5

Generation of an Array Device with Electrodes Under the Supported Bilayers

This example describes the making of silicon electrodes covered by a thin layer of silicon dioxide. Bond pads may be used to connect wires to the silicon electrodes.

A. Wafers

Silicon-on-oxide wafers were purchased from Ibis Technology Corporation, Danvers, Mass. The wafers are 100 mm in diameter and approximately 500 μm thick. As supplied by the manufacturer, the wafers have a ~0.4 μm thick silicon dioxide layer buried under a ~0.2 μm thick layer of pure silicon, which forms the top surface of the wafer.

B. Pre-resist Clean and Resist Coating

The wafers were cleaned with a conventional RCA cleaning procedure (Kern and Puotinen, 1970; Wolf and Tauber, 1986, p. 516), baked at 150° C. for 30 minutes, and coated with 1 μm of photoresist (Shipley S-1813) using conventional spin coating with a Silicon Valley Group (SVG) track coater system.

C. Exposure and Development

The mask pattern was exposed using an 8 second exposure on a Karl Suss MA-4 contact mask aligner with an electron beam master mask consisting of chrome patterns on a quartz substrate. The wafers were then soaked in chlorobenzene for 15 minutes before developing with standard TMAH (tetramethylammonium hydroxide) based developer (Shipley) using a Silicon Valley Group track developer system.

D. Etch and Thin Oxide Growth

The electrode patterns were etched into the top silicon layer using a conventional fluorine based plasma etch (Wolf and Tauber, 1986), which selectively etches silicon, but not silicon dioxide. The gases used in the plasma etch were $SF_6$, $O_2$, and $CHF_3$. Following a second RCA clean, a thin oxide was grown at 1000° C. in a steam oven to a thickness of 0.1 μm.

E. Pattern for Bond Pads

Another RCA clean is performed and a new layer of resist is deposited as described above. A new pattern, which defined openings in the oxide layer grown in the previous step, was transferred to the resist by photolithography as described above and the exposed resist was developed as described above.

F. Etch Openings for the Bond Pads

The wafers were etched in an Applied Materials (Santa Clara, Calif.) reactive ion etcher to open holes in the top oxide layer so that contacts to the underlying silicon layer could be made for bond pads.

G. Evaporate Gold

A 0.3 μm layer of gold was evaporated on the wafer before the resist from the previous step was removed. This gold was then lifted off with acetone, resulting in gold bond pads located in the holes which were etched in the previous step.

EXAMPLE 6

Machine Printing Discrete Fluid Membrane Arrays on Surfaces

Surface detector array devices of the present invention have been developed by Proteomic Systems, Inc. These devices, known as MembraneChips™, are important tools for studying membrane associated to study drug targets. The earliest developmental work on these MembraneChips™ involved construction of fluid membrane arrays by hand to study biological membranes. Later work allowed the construction of gradient arrays that permitted continuously variable changes of membrane composition across the surface of the array. While these results clearly demonstrated proof of concept for the surface detector array devices, the approaches are laborious and therefore not cost-effective for commercial production, and imposed limitations especially with respect to the ability to address discrete, predetermined membrane compositions onto the surface of the array, while maintaining the advantages of small feature size.

Developing an automated process for fabricating the microarrayed fluid bilayers onto a MembraneChip™ surface is an important technological accomplishment that is prerequisite for large scale production of these devices. It also enables the reproducible construction of high quality arrays of fluid membranes having discrete, predetermined membrane compositions at each feature or corral.

Figure 8:
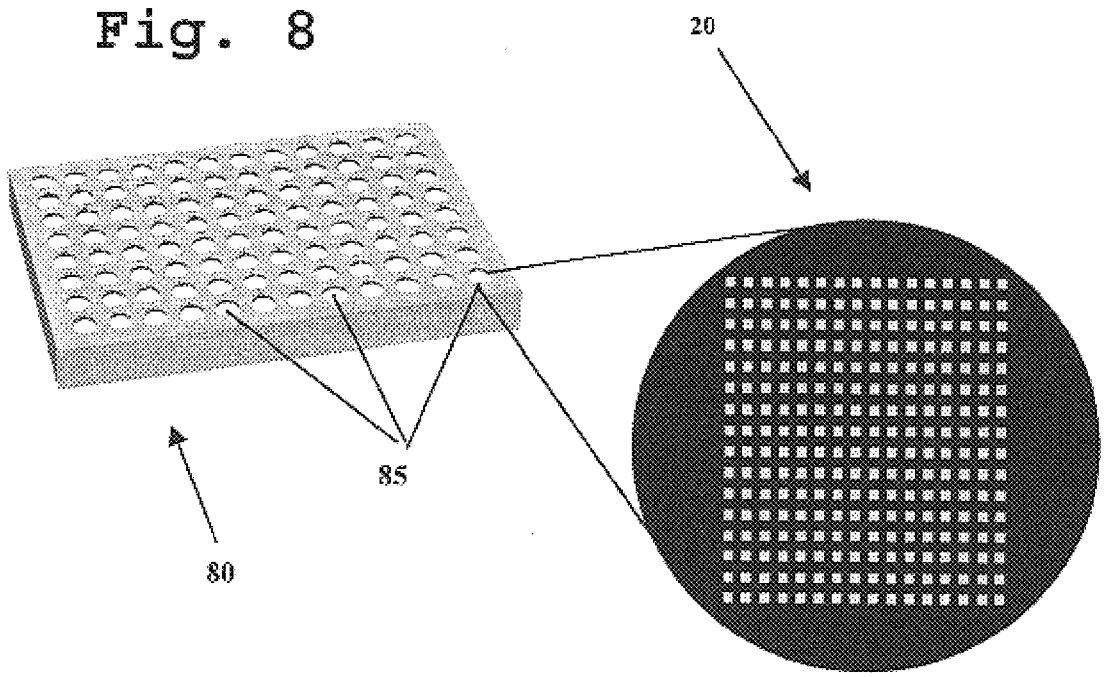
FIG. 8 depicts a well plate having surface detector array devices of the present invention at the bottoms of the wells.

Arrays of discrete fluid membranes 20 (FIG. 8) may be deposited into wells 85 of a multi-well plate 80 (e.g., a plate having 24, 48, 96, 384, 1536, or more wells), allowing for parallel and controlled exposure of all the corrals within an array to a single test agent or ligand, and for exposure of different arrays (each located in a separate well) to a different test agent or ligand. The ability to collect information from all discrete membrane array elements at once is extremely powerful, as exposure of all corrals to the same bulk solution containing a test agent or ligand provides the cleanest and the most controlled way to collect results. Use of multi-well plates allows rapid screening of many different test agents or ligands. Assay designs combining the surface detector array devices of the present invention with multi-well plates therefore enable N×M data points to be rapidly collected where N is equal to the number of corrals on a surface detector array device and M is equal to the number of wells in the multi-well plate.

In this example, we describe the use of a microarrayer to construct arrays of discrete functional membranes in a surface detector array device. The machine-made MembraneChips™ can be used to study drug targets in membranes, as detailed in the examples that follow.

Vesicle/proteovesicle spreading solutions were prepared essentially as described in the Materials and Methods sections A, B, and C, supra.

Patterned support grids were prepared essentially as described in Example 1, with the following modifications. After piranha cleaning the surface, the patterned support grids were stored under deionized water for at least six days. Selective surface modifications occur during this time. These modifications are important for microarrayer-based construction of discrete membrane arrays on the surface of the support.

The microarrayer was optimized for MembraneChip™ fabrication using the following parameters. The microarrayer used was a Cartesian, MicroSys™ Model 4100-2SQ, Irvine, Calif. operated with Cartesian, AxSys™ version 79.12 software, Irvine, Calif. using the following software settings:
Dispense type: Software programs for two different methods for dispensing were written. They are called "Direct" and "Touch-off." Both dispense types were successfully implemented using the parameters described below.
Z origin: 0.00 mm (31.00 mm away from the surface of the patterned support grid)
Tip height at dispensing:
 Direct: ~1500 microns away from the surface (29.50 mm from Z origin).
 Touch-off: Drops of samples were formed at the end of the tips at ~1500 microns from the surface (29.50 mm from Z origin). The tips then slowly were moved closer to the surface to ~160 microns away from the surface (30.84 mm from Z origin) to allow the drops of sample to touch the surface but without touching the tip to the surface.
Pre-dispense: Pre-dispensing prepares and conditions the tips for actual dispensing.
 Direct: Dispense 10 times then vacuum dry, dispense again 8 times then vacuum dry, then dispense again 4 times then vacuum dry.
 Touch-off: Dispense 2 times then vacuum dry, dispense again 2 times then vacuum dry, then dispense again 10 times then vacuum dry.
Open time of valve for dispensing: use AxSys™ version 79.12 software-suggested value (i.e., for above parameters ranging from 200 μsec to 3 sec.)
Syringe speed:
 Start: 0.04 mol/sec
 Stop: 0.5 sec/sec
 Acceleration: 12 mL/sec$^2$
The MembraneChip™ was fabricated using the microarrayer, following the steps summarized below.
 1. Prime system with isopropanol to rid system of air bubbles and then with deionized water to rid trace of isopropanol
 2. Wash and vacuum dry tips (3 times)
 3. Vent to relieve pressure in system
 4. Move ceramic tips (3 mm diameter, 190 micron orifice size) to source well (96/384-well plate)
 5. Aspirate (typically ~50 μL) of lipid/proteovesicles from source 96 well (working volume range 20–300 μl) or 384 well plate (working volume range 10–100 μl)
 6. Vent to relieve pressure in system
 7. Pre-pressurize to build positive pressure in the system by dispensing once the actual dispense volume without opening valve
 8. Pre-dispense as described above
 9. Actual dispense vol.: 10–90 nL—Dispense to the prepared MembraneChips™ patterned support grids
 10. Fill up the chip holder with deionized water
 11. Purge with deionized water
 12. Wash and vacuum dry tips The parameters of the program are finely optimized to ensure that the arrayer creates functional and fluid membrane bilayers. MembraneChips™ were submerged under water immediately after the microarrayer finished printing membranes on chips (step 9, supra). A larger orifice size tip (508 microns) was used to fill up the chip holder with deionized water. After membrane formation, even a brief exposure to air instantaneously destroys their structure, resulting not only in a lack of membrane fluidity but also disrupting proteins embedded in or associated with biological membranes. Membrane arrays therefore must be kept under water at all times following fabrication.

Two types of dispensing methods were used to construct MembraneChip™ arrays, as described above. With the "touch-off" technique, drops of lipid vesicles were formed at the end of the tips first, and then these drops were slightly touched to the surface to create a lipid bilayer. The bead of water stays as nicely round spots over the bilayer protecting it until the chip holder is filled with water. The second technique we call "direct dispense". In the direct dispense technique, lipid vesicle solution samples are dispensed by ejection from the tips at a small distance (e.g., about 150 microns) right above each corral. Sample spreads rapidly across the surface in a thinner layer. Here again the bilayer formed is protected by a thin layer of water. Both techniques can be used to create functional membranes.

Figure 9:
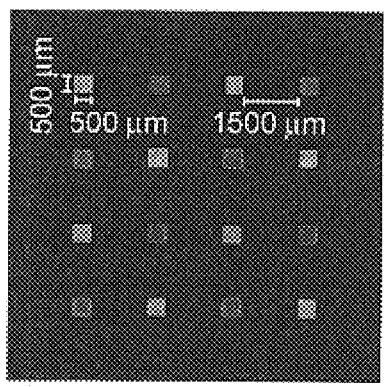
FIG. 9 depicts a surface detector array device of the present invention comprising two distinct lipid compositions arrayed in a "checkered board" pattern on the surface of the device.

The microarrayer successfully constructed a 'Checkered Board' pattern onto MembraneChips™ (FIG. 9) using two different types of small unilamellar vesicles, egg phosphatidylcholine (Avanti Polar Lipids, Alabaster, Ala.) with 1 mole percent N-(Texas Red sulfonyl)-1,2-dihexadecanoyl-sn-glycero-3-phosphoethanolamine(from Molecular Probes, Eugene, Oreg.) and egg PC with 1 mole percent 16:0–12:0 NBD-phosphatidylglycerol (from Avanti Polar Lipids, Alabaster, Ala.). The MembraneChips™ prepared in this experiment have 500 micron squares corrals with 1500 micron separation between the corrals. The red and green observed in the corrals are fluorescence from the NBD- and Texas Red-conjugated containing lipid bilayers, respectively. The colors in the corrals remain pure green or red. No mixing of colors occurs, proving the ability of the optimized microarrayer to construct an array of discrete, isolated membranes.

EXAMPLE 7

Machine-Made MembraneChips™ Have Fluid Membranes

Figure 10:
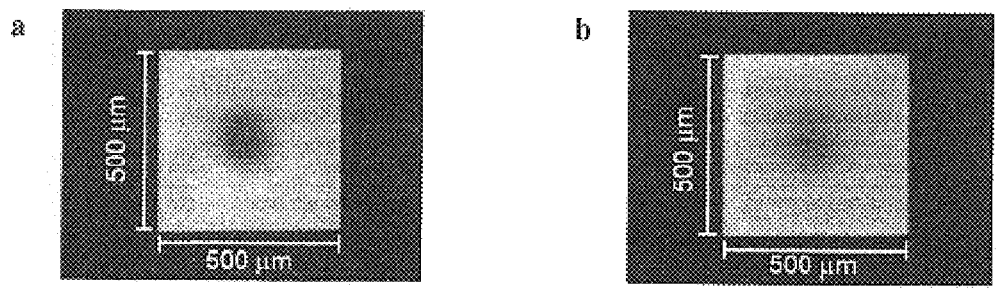
FIGS. 10a and b depict results of a fluorescence recovery after photobleaching (FRAP) experiment on a corral composed of egg phosphatidyl choline (PC) and 1 mole percent 16:0–12:0 NBD-phosphatidyl glycerol.

Fluorescence recovery after photobleaching (FRAP) experiments were performed on representative corrals from the NBD-labeled (FIG. 10) and Texas Red-labeled (data not shown) membranes in the MembraneChip™ fabricated by the microarrayer. In one of the corrals an approximately 100 micron/millimeter diameter spot was photobleached by a 2 minute illumination with a 100 W mercury arc lamp (Ushio Inc., USH-102DH, Tokyo, Japan) directed through the aperture diaphragm (FIG. 10a). After photobleaching, extensive diffusion results in fluorescence recovery within the corral (see FIG. 10b, taken 10 minutes after irradiation), proving the fluidity of the membranes in the MembraneChip™ arrayed by the microarrayer.

EXAMPLE 8

Cholera Toxin Binds Specifically to Ganglioside GM1 on the MembraneChip™

The surface of the MembraneChip™ is designed to expose all features (i.e., corrals) of the array to a single reagent at the same time. To demonstrate this quality, a MembraneChip™ experiment was performed (FIG. 11) to show that the arrayed membranes can be used as specific targets for assaying the binding of test agents. A MembraneChip™ was constructed according to the automated methods described in Example 6. In a four by four array having 500 micron$^2$ features (i.e. corrals) all but one of the corrals was arrayed with a solution containing 99 mole percent egg phosphatidylcholine with 1 mole percent NBD- phosphatidylglycerol. The last corral 110 (third column, third row, origin at top left corner) was arrayed with 98 mole percent egg phosphatidylcholine, 1 mole percent NBD- phosphotidylglycerol and 1 mole percent unlabeled GM1. When observed under a fluorescence microscope (Nikon Instruments, Inc., Nikon Eclipse E400, Melville, N.Y.) outfitted with the appropriate FITC filter set (Nikon Instruments, Inc., 96106807B-2A, Melville, N.Y.), the chip appeared uniformly green (data not shown).

Figure 11:
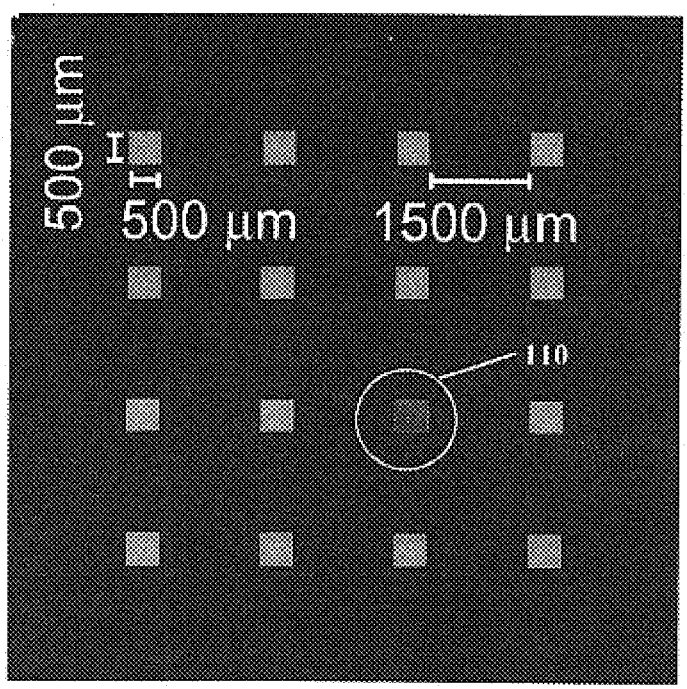
FIG. 11 depicts the result of an experiment using a surface detector array device of the present invention to illustrate that cholera toxin specifically binds ganglioside GM1.

Cholera toxin very specifically binds to the ganglioside GM1. The MembraneChip™ was able to detect this specific interaction. The MembraneChip™ was incubated with 1 ml of 2 µg/ml Texas Red-labeled cholera toxin (Molecular Probes Eugene, Oreg.) in phosphate buffered saline for 1 hour at room temperature. Following incubation, the MembraneChip™ was washed by removing the cholera toxin-containing solution, and 1 ml of phosphate buffered saline at room temperature was added. The wash step was repeated 4 more times. Only the corral containing the 1 mole percent GM1 bound cholera toxin. When imaged with a fluorescence microscope, the GM1-containing corral 110 appeared red, while the other corrals, lacking GM1, do not bind any cholera toxin and so remained green (FIG. 11).

The successful automated construction of MembraneChip™ microarrays displaying functional membranes on a surface expands the ability to study, in massively parallel experiments, native and artificial cell membranes, including cell membranes with associated proteins that are drug targets. These microarrayed MembraneChips™ therefore are valuable tools for high-throughput, low cost, and extremely accurate drug screening, optimization, and target identification directed at membrane components.

EXAMPLE 9

Analyses of G-Protein Coupled Receptors using MembraneChips™ Introduction

The majority of drug targets are membrane proteins, such as G-protein coupled receptors (GPCRs). For example, 60% of all prescription pharmaceuticals target GPCRs. These proteins merit such attention because they mediate a large number of cellular actions that are initiated by ligands, such as hormones and neurotransmitters, binding to GPCRs. Ligand binding to GPCRs mediate a wide range of physiological functions relating to metabolism, cell growth, and neurotransmission.

Recently, with the aid of human genome data, about 1,000 GPCRs have been discovered yielding a huge opportunity to create drugs for new targets. These discoveries have created a new dilemma in pharmaceutical drug development in choosing the best target to evaluate. Methods used to date in drug development rely mainly on linear one-to-one processes and are not appropriate for parallel evaluation of multiple targets. To fully exploit the recent GPCR discoveries, new methods for handling membrane proteins in parallel are required. Proteomic Systems' MembraneChip™ platform addresses this need. The MembraneChip™ can be used to display numerous active GPCRs in their native membrane environment in an array format such that drugs can be tested against a multitude of GPCRs in a highly parallel, multiplexed manner.

This example describes experiments carried out using the MembraneChips™ of the present invention. The data clearly demonstrate that the MembraneChip™ technology provides a system for parallel analysis of GPCRs in pharmaceutical drug development.

MembraneChip™ GPCR Assays

MembraneChips™ can be used to display any number of GPCRs in a parallel format. GPCR membrane preparations were purchased from Stratagene (La Jolla, Calif.) or Packard BioScience (Meriden, Conn.). 1:1 ratios of membrane preparations to egg phosphatidylcholine (Avanti Polar Lipids, Alabaster, Ala.) vesicle preparations, prepared using the procedure described in Material and Methods, were incubated at 37° C. over night and used as spreading solutions. GPCRs were then arrayed into designated corrals on a chip using a microarrayer, as described in Example 6. The coordinates of each GPCR on the chip were tracked. The lipid bilayer in which the GPCRs are embedded is biologically active; the GPCRs are functional and oriented in a native or native-like membrane environment.

A fluorescence based detection system was employed to detect binding of ligands to GPCRs. The ligands were labeled with the fluorescent dyes BODIPY TMR or BODIPY 558/568 (Molecular Probes, Eugene, Oreg.). All ligands were dissolved with 50 mM Tris HCl (pH 7.2), 12.5 mM $MgCl_2$, 2 mM EDTA unless otherwise noted. The saturation curve was generated following a standard protocol as set forth in *Methods in Molecular Biology, Receptor Binding Techniques*, Humana Press, Totowa, N.J., 1999, p.41–42, incorporated herein by reference. The β-adrenergic subtype 1 Receptor (AR-β1, Packard BioScience, Meriden, Conn.) was incubated with 42 nM, 15 nM, 10 nM, 5 nM, 0.04 nM of BODIPY TMR CGP12177 (Molecular Probes, Eugene, Oreg.) in a total volume of 1 ml for 1 hour at room temperature. Each well, containing a MembraneChip™ was washed three times with 1 ml of 50 mM Tris HCl (pH 7.2), 12.5 mM $MgCl_2$, 2 mM EDTA at room temperature. All other assays were performed similarly to the saturation curve.

The competitive binding studies were also carried out under similar conditions to the saturation experiments following a standard protocol as set forth in *Methods in Molecular Biology, Receptor Binding Techniques*, Humana Press, Totowa, N.J., 1999, p.42–43. Briefly, fluorescent ligand and unlabeled drug were dissolved in 50 mM Tris HCl (pH 7.2), 12.5 mM $MgCl_2$, 2 mM EDTA. The fluorescence intensities were measured after probing for 1 hour at room temperature in a total volume of 1 ml. Each well was washed three times with 1 ml of 50 mM Tris HCl (pH 7.2), 12.5 mM $MgCl_2$, 2 mM EDTA at room temperature.

Binding of the labeled ligands to specific GPCRs was measured by the presence of fluorescent signal in the membrane corral(s) where the specific GPCR(s) reside(s). Competitive binding assays were designed and carried out to identify the relative affinity of a drug (or drug candidate or other test agent) for particular GPCRs. Unlabeled drug is mixed with a fluorescent ligand and incubated with the MembraneChip™. Alternatively, a fluorescent ligand may first be incubated with the MembraneChip™, the specific binding of the ligand is determined by capturing a fluorescence image and establishing the absolute or relative fluorescence signal associated with the corral(s), after which time the MembraneChip™ is incubated with an unlabeled drug (or drug candidate or other test agent). If the unlabeled compound competes with the fluorescent ligand for a binding site on the GPCR, the fluorescent ligand binding to the GPCR is displaced, diminishing the fluorescence in the corral containing that GPCR. The decrease in signal is considered a positive "hit" for the drug being tested against that specific GPCR.

Binding of ligands to GPCRs displayed on MembraneChips™ was monitored using a fluorescence microscope (Carl Zeiss, Inc., Axiovert 100, Thornwood, N.Y.). Images from the microscope were captured (Roper Scientific Germany, CoolSNAP, Munich, Germany and Roper Scientific Germany, CoolSNAP Software Version 1.1, Munich, Germany), and integrated fluorescence density was converted into a quantitative number, termed Relative Fluorescence Units (RFUs), using a publicly available software package, Scion Image (Scion Corporation, Scion Image Beta 4.0.2, Frederick, Md.).

Results

One key feature of the MembraneChip™ is that substantially less GPCR is required for each data point compared to other traditional assays (filter binding and scintillation proximity assay (SPA)) used in drug development today. In Table 1 the amount of membrane and a specific GPCR, AR-β1, required for a typical filter binding assay and SPA are calculated and compared to what is required for assays on the MembraneChip™. This is especially significant because obtaining quantities of GPCRs is often time consuming and difficult. Furthermore, often GPCRs represent the largest percentage of total cost in developing drug screening and optimization assays. As Table 1 illustrates, MembraneChips™ provide a greater than a 300 fold reduction in the amount of GPCR required per data point.

TABLE 1

Amount of membrane and GPCR (AR-β1) used per assay.

| Assay Type | µg of membrane | Femtomoles of AR-β1[1] |
|---|---|---|
| MembraneChip™[2] | <0.2 | <0.3 |
| Filter Binding Assay[3] | 21.5 | 36.6 |
| SPA[4] | 19 | 32.3 |

[1]Packard BioScience (Meriden, CT) cat. number 6110106, lot number 6110106X-21, specific activity: 1.8 pmol/mg membrane protein.
[2]Using 1 $mm^2$ corrals.
[3]Using recommended assay conditions with 5 mm diameter GF/C filters as outlined on technical data sheet for Packard BioScience AR-β1, lot number 6110110X-24.
[4]As outlined in SPA G-protein coupled receptor assay (Amersham Biosciences, RPNQ0210, Piscataway, NJ)

Figure 12:
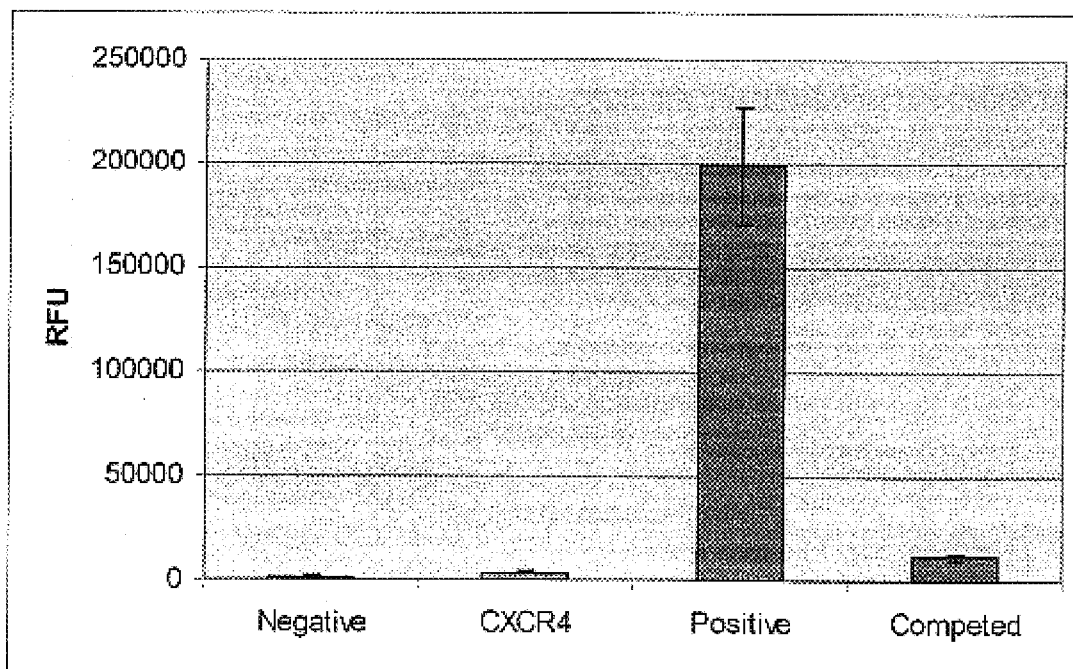
FIG. 12 depicts results of a β1 adrenergic receptor (AR-β1) competition assay showing the suitability of the surface detector array devices of the present invention for use in drug-screening and optimization applications.

Competitive binding assays were developed using two GPCRs, the β-adrenergic subtype 1 Receptor (AR-β1, Packard BioScience, Meriden, Conn.) (FIG. 12 and Table 2) and the muscarinic receptor subtype M1 (M1, Packard BioScience, Meriden, Conn.) (Table 2). This type of experiment may be used for drug optimization. A MembraneChip™ surface corral arrayed with a lipid only control (negative control) was probed with a 100 nM solution of the AR-β selective fluorescent antagonist analog, BODIPY TMR CGP 12177 (Molecular Probes, Eugene, Oreg.). Fluorescence on the surface was extremely low (FIG. 12 and Table 2 "Negative"). To assess the specificity of binding against other GPCRs, MembraneChips™ containing CXCR4 (CXC chemokine Receptor 4) were probed with the same concentration of BODIPY TMR CGP12177 (FIG. 12 and Table 2 "CXCR4"). A signal slightly higher than the negative control was obtained and was expected since this CXCR4 cellular membrane preparation also contains low endogenous levels of AR-β1. When MembraneChips™ containing cellular membrane preparations from cells over expressing AR-β1 were probed with 100 nM BODIPY TMR CGP12177, a large signal was observed (FIG. 12 and Table 2 "Positive"). Importantly, about 95% of the positive signal was competed out when 5 mM unlabeled AR-β selective antagonist, propranolol (Sigma, St. Louis, Mo.) was included with the 100 nM BODIPY TMR CGP12177 (FIG. 12 and Table 2 "Competed"), mimicking a drug hit.

Z' (Table 2) is a dimensionless figure of merit often used in evaluating high throughput screening (HTS) assays. See, "A Simple Statistical Parameter for use in Evaluation and Validation of High Throughput Screening Assays," *Biomolecular Screening*, 4: 67–73 (1999), incorporated herein by reference. A Z' value less than 0 is not acceptable according to commonly used industrial standards. The Z' for this set of 9 measurements from 3 independently performed experiments (3 chips×3 measuring sites per chip) is 0.43 (Table 2), which is comparable to values obtained using other commercial assays, which are in the vicinity of 0.5. The standard deviation for this set was 14% (Table 2).

Similar experiments were performed on another well-characterized GPCR, muscarinic receptor subtype M1 (Table 2). The fluorescent ligand used in this case was 15 µM BODIPY 558/568 Pirenzepine (Molecular Probes, Eugene, Oreg.), which is a subtype-selective fluorescent antagonist.

The competing drug was a receptor selective antagonist, scopolamine (1.3 μM, Sigma, St. Louis, Mo.). These data taken together demonstrate that MembraneChips™ can be used to establish ligand binding assays that display little cross reaction with other GPCRs. Furthermore, the data show that the MembraneChips™ perform in a manner acceptable for drug development processes.

Figure 14:
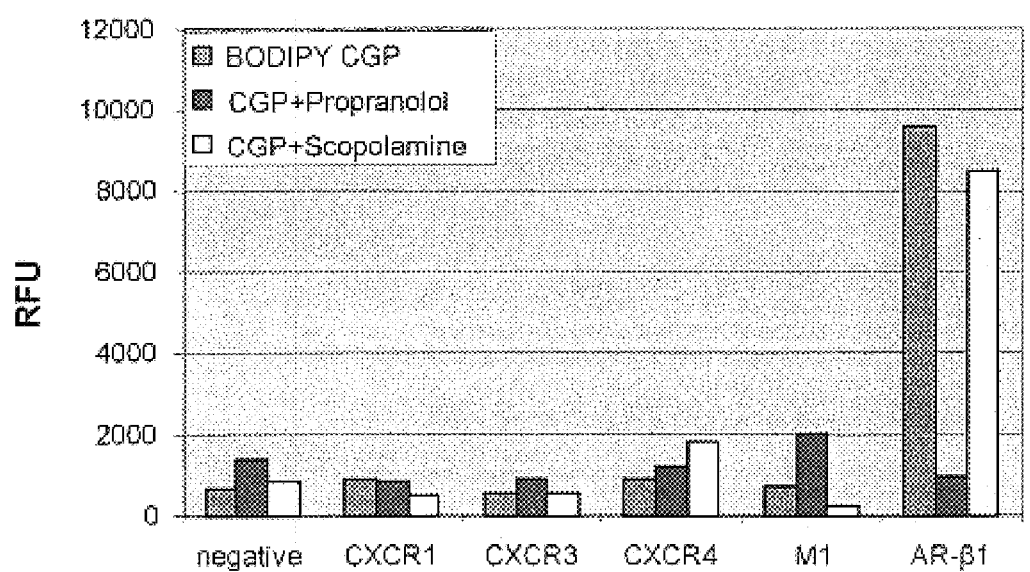
FIG. 14 depicts results of an experiment showing the utility of the surface detector array devices of the present invention for carrying out multiplexed assays.

TMR CGP12177 was seen to pure lipid, CXCR1, CXCR3, CXCR4, or M1 (FIG. 14). For lipid only ("negative"), CXCR1, CXCR3, and CXCR4 corrals, only negligible differences were observed when propranolol or scopolamine were added (FIG. 14). These results clearly demonstrate that GPCRs prepared on MembraneChips™ retain their natural biological specificity for ligands and drugs.

TABLE 2

Relative Fluorescence Units (RFU)[5] ± standard deviation, intensity in arbitrary units.

| Receptor | Negative | CXCR4 | Positive | Competed | Signal to Noise (S/N) | % Std Dev[6] | Z' |
|---|---|---|---|---|---|---|---|
| AR-β1 | 1,447 ± 208 | 3,796 ± 424 | 199,137 ± 28,494 | 11,484 ± 1,649 | 138x | 14 | 0.43 |
| M1 | 2,637 ± 1,846 | 8,788 ± 3,137 | 58,467 ± 4,911 | 16,266 ± 744 | 22x | 8 | 0.19 |

[5]Obtained by analysis with Scion Image Beta 4.0.2.
[6]For independently performed experiments.

Figure 13:
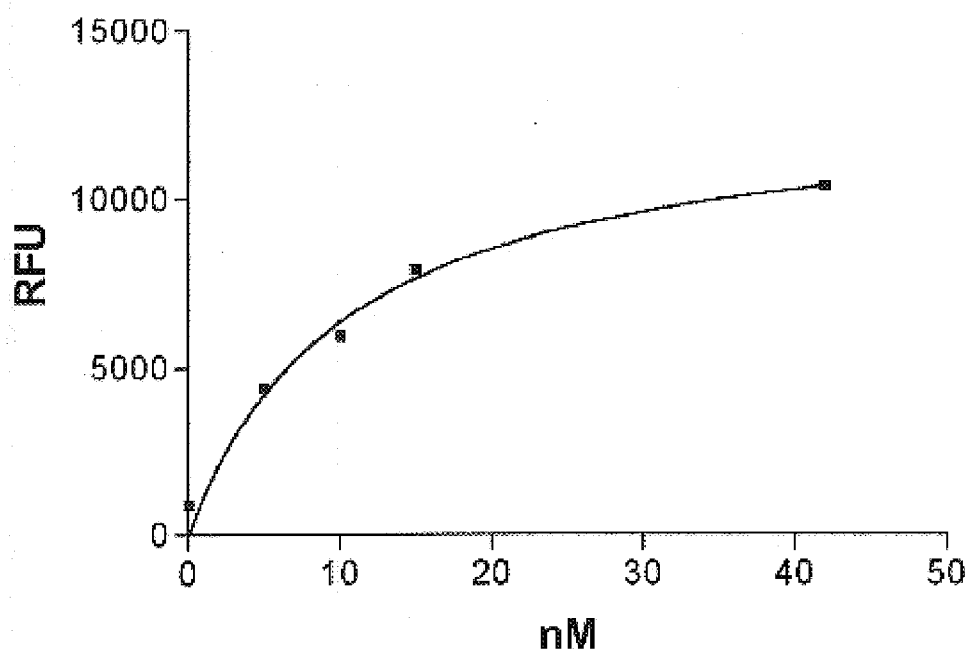
FIG. 13 depicts a dose-response curve for the binding of fluorescently labeled β1 adrenergic receptor antagonist BODIPY TMR CGP12177 to β1 adrenergic receptor on the surface detector array devices of the present invention.

Further experiments were performed to assess the capability of the MembraneChip™ system for determining dissociation constant values for a given drug compound. These dissociation constant values, $K_d$, are a measure of the binding affinity of the compound to its receptor. Standard saturation isotherm binding curves were determined according to the protocol outlined in *Methods in Molecular Biology, Receptor Binding Techniques*, Humana Press, Totowa, N.J., 1999, p.40–41. These experiments were performed using different concentrations of BODIPY TMR CGP12177 to probe for a fixed amount of AR-β1, a GPCR described above. The resulting saturation curve is shown in FIG. 13. Using curve fitting analysis (Graphpad, Prism version 3.0, San Diego, Calif.), the $K_d$ was determined to be 10 nM (FIG. 13), which is consistent with $K_d$s reported for other CGP12177 derivatives. This experiment was repeated, and a $K_d$ of 8 nM was determined (data not shown), which is well within the industry's acceptable range for reproducibility.

EXAMPLE 10

Multiplexed MembraneChip™ Assays

MembraneChips™ were developed to demonstrate the utility of the MembraneChip™ system for multiplexed GPCR assays. Multiplexed assays, in which multiple targets are present on a single substrate and simultaneously exposed to a test agent, allow for very accurate determinations of the relative affinities the test agent for the various targets on the substrate. A MembraneChip™ containing GPCRs, CXCR1, CXCR3, CXCR4, M1 and AR-β1, was fabricated according to the methods outlined in Example 6 and was probed with the AR-β1 specific ligand CGP12177, according to the methods outlined in Example 9. The fluorescence signal from 20 nM BODIPY TMR CGP12177 binding to AR-β1 is 22 times the average fluorescence from non-specific binding of the fluorescent ligand to pure lipid (FIG. 14, "negative") CXCR1, CXCR3, CXCR4, and M1 (FIG. 14, "BODIPY CGP" bars). Binding of the fluorescently-labeled CGP12177 to AR-β1 was competed by addition of unlabeled 5 mM propranolol, as expected (FIG. 14, "CGP+Propranolol" bar for AR-β1 column). Little decrease in fluorescence was seen upon addition of 15 mM scopolamine, an agent that has high affinity for M1 receptors but not for AR-β1 (FIG. 14"CGP+Scopolamine" bar for AR-β1 column).

Figure 15:
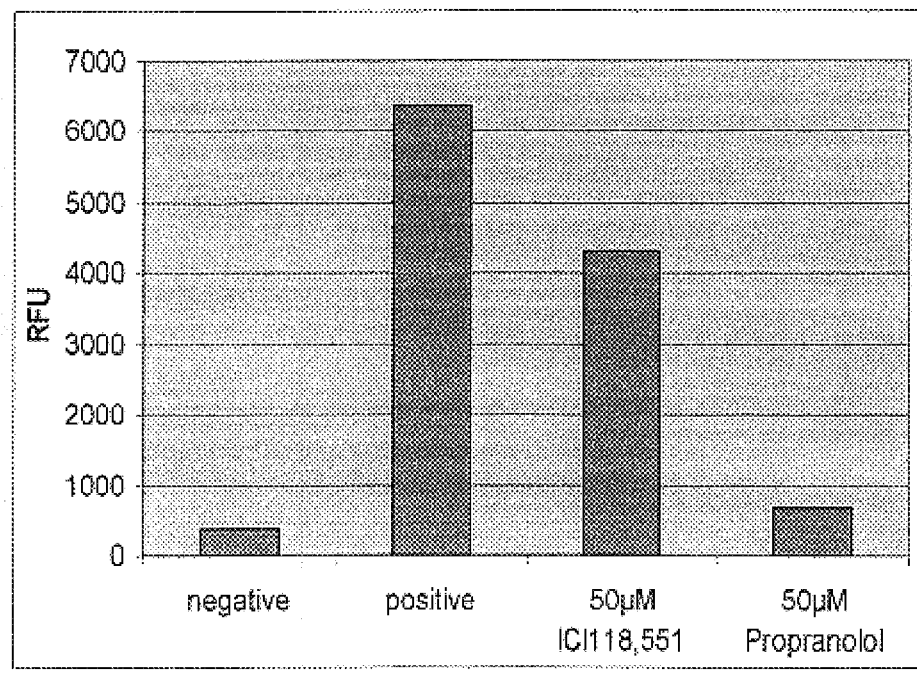
FIG. 15 depicts results of an experiment illustrating use of a surface detector array device of the present invention in a competition assay to estimate the affinity of different compounds for AR-β1.

The binding of CGP12177 was extremely specific for AR-β1. As stated above, very little binding of BODIPY MembraneChips™ also can be used to estimate the affinity of different compounds to GPCRs. Competitive binding assays were established using the fluorescent ligand CGP12177 and MembraneChips™ displaying AR-β1. The fluorescent signal and hence binding of the ligand shown in FIG. 15 "positive" was competed with drugs that are known to have varying affinities for AR-β1. In FIG. 15, "negative" is lipid only control corral, "positive" is AR-β1 corral. The drugs ICI118,551 and propranolol both bind to AR-β1 but with different affinities, $K_d$s ~200 nM and ~1 nM, respectively. In our experiment, 50 μM ICI118,551 competed out approximately 30% of the fluorescent signal while at the same concentration, propranolol competed out almost 90% of the signal (FIG. 15). These results are consistent with the known $K_d$ for ICI118,551 and propranolol binding to AR-β1, and illustrate that differential binding capabilities of different drugs to a single GPCR can be measured using the MembraneChip™ technology.

Figure 16:
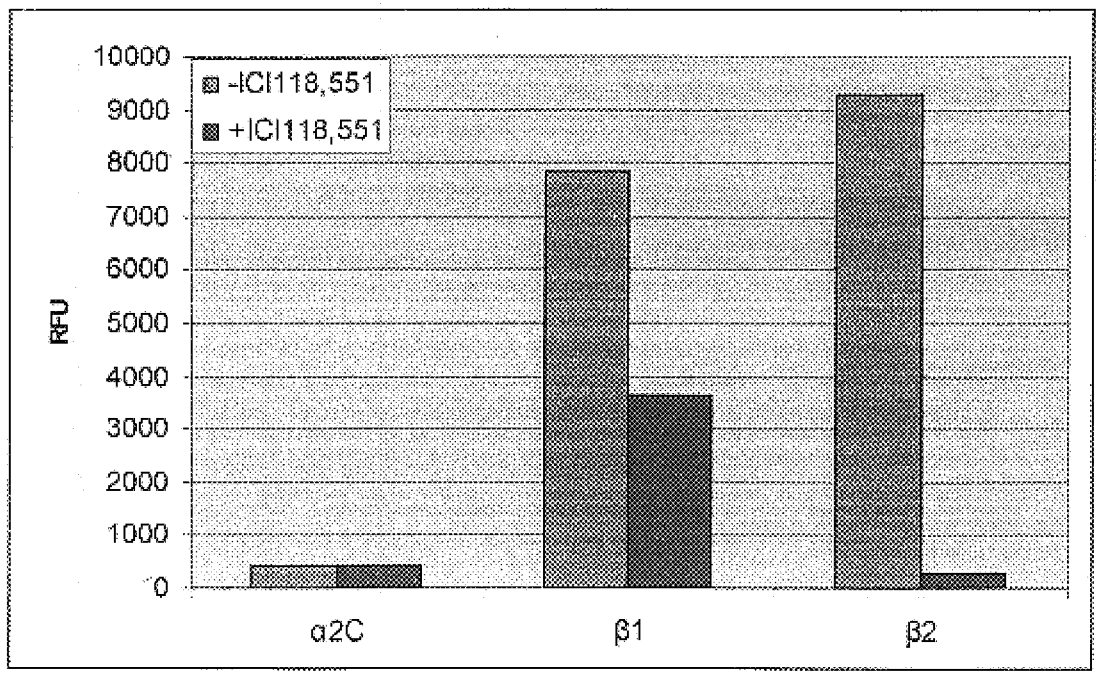
FIG. 16 depicts results of an experiment illustrating use of a surface detector array device of the present invention in a competition assay to estimate the affinity of different adrenergic receptors for the compound ICI118,551.

Further studies were performed to test the feasibility of estimating differences in the affinity of a compound to a family of adrenergic receptors, namely, AR-α2C, AR-β1, and AR-β2 (FIG. 16). Selectivity of a drug for a specific family member is crucial for maximizing therapeutic effect while minimizing undesirable side effects. BODIPY TMR CGP12177 is an AR-β family selective antagonist. This selectivity for AR-β is demonstrated by the relative BODIPY TMR CGP12177 fluorescence signal in the AR-β1 and AR-β2 but not AR-α2C corrals (FIG. 16, "–ICI118,551" bars). Upon addition of ICI118,551, the BODIPY TMR CGP12177 fluorescence dramatically decreases for AR-β2 but only partially for AR-β1 corrals (FIG. 16, "+ICI118, 551" bars) because ICI118,551 binds with greater affinity to AR-β2 ($K_d$~1 nM) than to AR-β1 ($K_d$~200 nM). These results illustrate that the MembraneChip™ can be used to carry out multiplexed assays to characterize the relative binding affinity of a drug for different members of the same receptor family.

EXAMPLE 11

Antibody binding to Receptors arrayed on MembraneChip™

Figure 17:
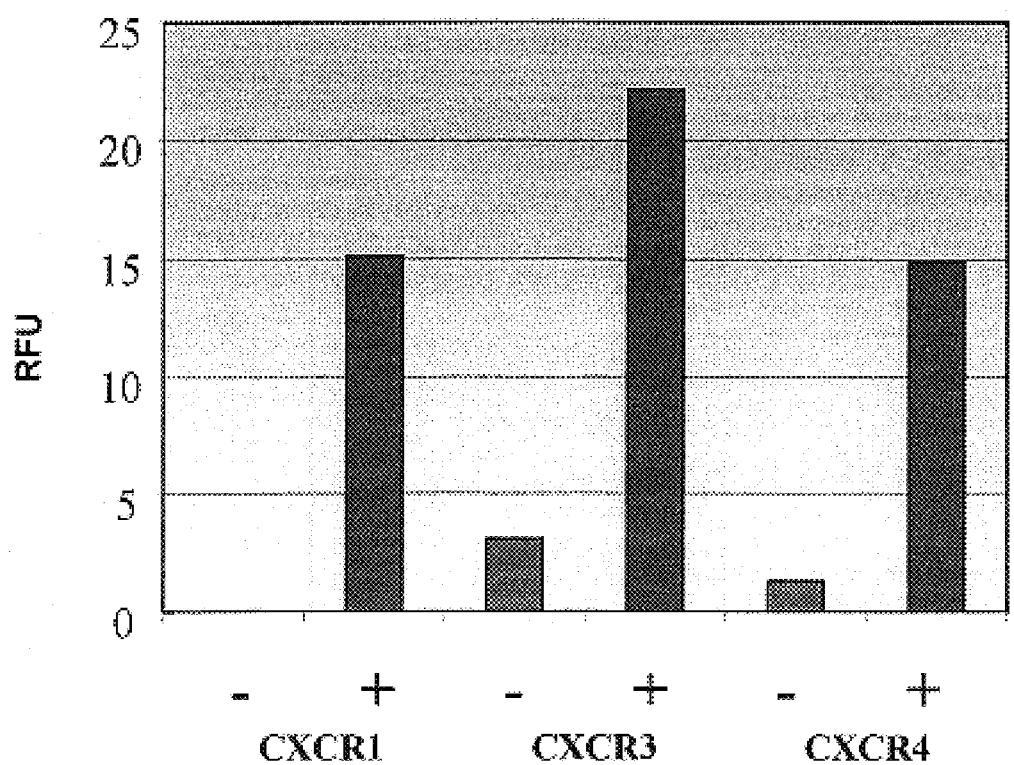
FIG. 17 depicts results of an experiment illustrating use of a surface detector array device of the present invention with labeled antibodies to recognize chemokine receptors incorporated into the surface detector array device.

Chemokine receptors, CXCR1, CXCR3, and CXCR4 (Stratagene, LaJolla, Calif.) were incorporated into proteoliposome vesicles as described above, and arrayed on the surface of a MembraneChip™ using the procedure described in Example 6. They were then detected by incubating the MembraneChip™ with fluorescently labeled antibodies recognizing each of the CXCRs (FIG. 17), washing the MembraneChip™, and capturing and processing the fluorescence micrograph image as described above. Statistically significant increases in Relative Fluorescence Units (RFU) compared to background (respectively "+" and "−" in FIG. 17) in locations where the GPCRs are placed proves that the structures of the antigenic sites on the receptors were preserved after arraying on the MembraneChip™ surface. This result illustrates that MembraneChips™ may be used to characterize antibody binding to antigens, and that antibody binding may be used to detect targets present on the MembraneChip™ surface.

Conclusion

Sensitive membrane assays have been adapted to the MembraneChip™. The assays are compact and compatible with robotic reagent handling systems, and enable screening of novel antagonists and agonists against discrete membrane arrays of receptors in a multiplexed format.

While the invention has been described with reference to specific methods and embodiments, it will be appreciated that various modifications may be made without departing from the invention. All references cited, including scientific publications, published patent applications, and issued patents, are herein incorporated by reference in their entirety for all purposes.

References

Allen, T. M., et al., in *Stealth Liposomes* Chapter 20 (D. Lasic and F. Martin, Eds.) CRC Press, Boca Raton, Fla., (1995).
Arnold, F. H., *Bio/Technol.* 9:151–156 (1991).
Ausubel, F. M., et al., *Current Protocols in Molecular Biology*, John Wiley and Sons, Inc., Media Pa. (1988).
Ballantyne, J. P., et al., *J. Vac. Sci. Technol.* 10:1094 (1973).
Barenholz, Y., et al., *Biochemistry* 16:2806–2810 (1977).
Blanchard, A., et al., *Biosensors & Bioelectronics* 11:687–690 (1996).
Brian, A. A., and McConnell, H. M., *Proc. Natl. Acad. Sci. USA* 81:6159 (1984).
Caras, et al., *Science* 238:1280–1283 (1987).
Case, et al., U.S. Pat. No. 5,192,507, issued Mar. 9, 1994.
Chan, P. Y., et al., *J. Cell Biol.* 115:245 (1991).
Cullen, D. C., et al., *Biosensors* 3:211–225 (1988).
Corsel, J. W., et al., *J. Colloid. Interface Sci.* 111:544–554 (1986).
Elender, et al., *Biosensors and Bioelectronics* 11:565–577 (1996).
Fodor, S. P. A., et al., *Science* 251:767 (1991).
Frey, W., et al., *Proc. Natl. Acad. Sci. USA* 93:4937 (1996).
Gitler, et al., U.S. Pat. No. 5,204,239, issued Apr. 20, 1993.
Groves, J. T., and Boxer, S. G., *Biophys. J.* 69:1972 (1995).
Groves, J. T., et al., *Biophys. J.* 71:2716 (1996).
Hamill, O. P., et al., *Pflugers Arch.* 391:85 (1981).
Haugland, R. P., in *Handbook of Fluorescent Probes and Research Chemicals*, 5th Ed., Molecular Probes, Inc., Eugene, Oreg. (1992).
Heath, T. D., *Biochem. et Biophys. Acta* 640:66 (1981).
Hillebrandt, et al., *Langmuir* 15: 8451–8459 (1999).
Jönsson, U., et al., *Colloids Surfaces* 13:333–339 (1985).
Kern, W. and D. A. Puotinen, "Cleaning solution based on hydrogen peroxide for use in semiconductor technology" RCA Review (June) p. 187 (1970).
Khüner, et al., *Biophys J.* 67:217–226 (1994).
Krutenat, Kirk-Othmer 3rd Ed., Vol. 15, pp. 241–274 (1986).
Liedberg, B., et al., *Z. Phys.* 4:299–304 (1983).
Lin, A. Y., et al., *Science* 249:677–679 (1990).
Malik, S., et al., *New J. Chem.* 18:299–304 (1994).
Martin, F. J., *Biochemistry* 20:4229 (1981).
Martin, F. J., *J. Biol Chem.* 257:286 (1982).
Martin, F. J., in *Specialized Drug Delivery Systems-Manufacturing and Production Technology*, (P. Tyle, Ed.) Marcel Dekker, New York, pp. 267–316 (1990).
McConnell, H. M., et al., *Biochim. Biophys. Acta* 864:95 (1986).
McHugh, et al., *Proc. Natl. Acad. Sci. USA* 92:8059–8063 (1995).
*Methods in Molecular Biology, Receptor Binding Techniques*, Humana Press, Totowa, N.J., 1999, p.41–42.
Nellen, Ph.M., and Lukosz, W., *Sensors Actuators* B1:592–596 (1990).
Osman, et al., U.S. Pat. No. 5,234,566, issued Aug. 10, 1993.
Petersen, K. E., *Proceedings of the IEEE* 70:420–457 (1982).
Plant, A. L., et al., *Anal. Biochem.* 226(2):342–8 (1995).
Sackmann E., Tanaka M., *Trends Biotechnol.* 18(2):58–64 (2000).
Sadler, D. M., et al., *Biochemistry* 23:2704–2712 (1984).
Salafsky, J., Groves, J. T., and Boxer, S. G., *Biochem.* 35:14773–14781 (1996).
Sambrook, J., et al., *Molecular Cloning: a Laboratory Manual*, Cold Spring Harbor Laboratory Press, Vol. 2, Cold Spring Harbor Laboratory Press, Cold Spring Harbor, N.Y. (1989).
Schild, H., et al., *Cell* 76:29–37 (1994).
Shnek, D. R., et al., *Langmuir* 10:2382–2388 (1994).
Sigal, G. B., et al., *Anal. Chem.* 68:490 (1996).
Steizle, M., and Sackmann, E., *Biochim. Biophys. Acta* 981:135 (1989).
Stelzle, M., et al., *J. Phys. Chem.* 97:2974–2981 (1993).
Sui, S. F., Urumow, T., and Sackmann, E., *Biochemistry* 27(19):7463–9 (1988).
Szoka, F., Jr., et al., *Ann. Rev. Biophys. Bioeng.* 9:467 (1980).
Taylor, et al., U.S. Pat. No. 5,192,507, issued Mar. 9, 1993.
Tiberio, R. C., et al., *Applied Physics Letters* 62:476–478 (1993).
Thompson, L. F., et al., Eds., "Introduction to Microlithography", ACS Symposium Series, Washington D.C. (1983).
Tomich, et al., U.S. Pat. No. 5,368,712, issued Nov. 29, 1994.
Tozeren, A., et al., *J. Cell Biol.* 116:997 (1992).
Vroman, L., and Adams, A. L., *Surface Sci.* 16:438–446 (1969)
Watts, T. H., and McConnell, H. M., *Ann. Rev. Immunol.* 5:461 (1987).
Wettstein, et al., *J. Exp. Med.* 174:219–228 (1991).
Whitehorn, et al., *Biotechnology* 13:1215–1219 (1995).
Wolf, S., and Tauber, R. N., *Silicon Processing for the VLSI ERA*, Vol. 1, Lattice Press, Sunset Beach, Calif. (1986).
Wong, A. P., Groves, J. T., *J Am Chem Soc..* 123(49):12414–5 (2001).
Xia, Y., et al., *Science* 273:347 (1996).
Zalipsky, S., et al., in *Poly (Ethylene Glycol) Chemistry: Biotechnical and Biomedical Applications* (J. M. Harris, Ed.) Plenum Press, pg. 347–370 (1992a).
Zalipsky, S., et al., *Biotechnol. Appl. Biochem.* 15:100 (1992b).
Zalipsky, S., *Bioconjugate Chemistry* 4(4):296–299 (1993).
Zalipsky, S., et al., *FEBS Letters* 353:71–74 (1994).
Zalipsky, S., in *Stealth Lipsomes* Chapter 9 (D. Lasic and F. Martin, Eds.) CRC Press, Boca Raton, Fla., (1995).

We claim:

1. A method for fabricating a surface detector array device, comprising the steps of:
providing a substrate having a surface defining a plurality of distinct bilayer-compatible surface regions separated by one or more bilayer barrier regions, wherein said bilayer-compatible surface regions and said bilayer barrier regions are formed of different materials;
providing a first suspension of lipid-bilayer vesicles having a first composition;
providing a second suspension of lipid-bilayer vesicles having a second composition;
transferring an aliquot of said first suspension to a first of said plurality of distinct bilayer-compatible surface regions;
transferring an aliquot of said second suspension to a second of said plurality of distinct bilayer-compatible surface regions;
incubating said substrate with said first and said second suspension to form a first lipid bilayer expanse stably localized above said first distinct bilayer-compatible surface region, and a second lipid bilayer expanse stably localized above said second distinct bilayer-compatible surface region, wherein each of said expanses is localized above each of said surface regions in the absence of covalent linkages between each of said lipid bilayer expanses and each of said bilayer-compatible surface regions, and is separated therefrom by an aqueous film interposed between said bilayer-compatible surface regions and said corresponding lipid bilayer expanses; and
establishing a bulk aqueous phase above said lipid bilayer expanses.

2. The method of claim 1, wherein said first composition differs from said second composition.

3. The method of claim 1, wherein said substrate comprises between about 10 and about 100 distinct bilayer-compatible surface regions.

4. The method of claim 3, wherein said substrate comprises at least about 2500 distinct bilayer-compatible surface regions.

5. The method of claim 4, wherein said substrate comprises at least about 25,000 distinct bilayer-compatible surface regions.

6. The method of claim 5, wherein said substrate comprises at least about 2.5 million distinct bilayer-compatible surface regions.

7. The method of claim 1, wherein the bilayer-compatible surface regions are separated from one another by bilayer barrier regions that are between about 1 $\mu$m and about 10 $\mu$m in width.

8. The method of claim 1, wherein said first composition further comprises a biomolecule.

9. The method of claim 8, wherein said biomolecule is selected from the group consisting of a transmembrane receptor and an ion channel.

10. The method of claim 9, wherein the biomolecule is covalently attached to a lipid molecule.

11. The method of claim 1, wherein said transferring steps are automated.

12. The method of claim 1, wherein said transferring steps comprise generating drops of said first and said second suspensions and touching said drops to said respective first and said second bilayer-compatible surface regions.

13. The method of claim 12, wherein each of said drops comprises less than 100 nl.

14. The method of claim 13, wherein each of said drops comprises less than 15 nl.

15. The method of claim 1, wherein said transferring steps comprise ejecting aliquots of said first and second suspensions across air spaces and onto said respective first and second bilayer-compatible surface regions.

16. The method of claim 15, wherein each of said ejected aliquots comprises less than 100 nl.

17. The method of claim 15, wherein each of said ejected aliquots comprises less than 15 nl.

18. An apparatus for fabricating a surface detector array device, comprising:
a platform for receiving a substrate, said substrate having a surface defining a plurality of distinct bilayer-compatible surface regions separated by one or more bilayer barrier regions, wherein said bilayer-compatible surface regions and said bilayer barrier regions are formed of different materials;
a source of a first suspension of lipid-containing vesicles or liposomes having a first composition;
a source of a second suspension of lipid-containing vesicles or liposomes having a second composition;
means for transferring an aliquot of said first suspension to a first of said plurality of distinct bilayer-compatible surface regions and for transferring an aliquot of said second suspension to a second of said plurality of distinct bilayer-compatible surface regions; and
a source of a bulk aqueous phase used to cover said fabricated surface detector array device.

19. The device of claim 18, further comprising a chamber for controlling one or more environmental parameters in the vicinity of the substrate surface.

20. The device of claim 19, wherein said parameters are selected from the group consisting of temperature, relative humidity, pressure, and illumination.

21. The device of claim 18, further comprising a microprocessor operatively programmed to control the relative movement between said stage and said transfer means.

22. A multiplexed assay, comprising the steps of:
providing a surface detection array device, said device comprising
a substrate having a surface defining a plurality of distinct bilayer-compatible surface regions separated by one or more bilayer barrier regions, said bilayer-compatible surface regions and said bilayer barrier regions being formed of different materials,
a first lipid bilayer expanse having a first composition and stably localized above a first of said plurality of distinct bilayer-compatible surface regions,
a second lipid bilayer expanse having a second composition different from said first composition and stably localized above a second of said plurality of distinct bilayer-compatible surface regions,
wherein each of said expanses is localized above each of said surface regions in the absence of covalent linkages between each of said lipid bilayer expanses and each of said bilayer-compatible surface regions, and is separated therefrom by an aqueous film interposed between said bilayer-compatible surface regions and said corresponding lipid bilayer expanses;
contacting said device with a bulk aqueous phase comprising a test agent; and
assaying an interaction between said test agent and said first composition and an interaction between said test agent and said second composition.

23. The method of claim 22, wherein said first composition comprises a first biomolecule, and said second composition comprises a second biomolecule.

24. The method of claim 23, wherein said biomolecules are selected from the group consisting of a transmembrane receptor and an ion channel.

25. The method of claim 23, wherein said first and said second biomolecules are different members of a receptor protein family.

26. The method of claim 22, wherein said first composition comprises a first lipid and said second composition comprises a second lipid.

27. The method of claim 22, wherein each of said first and said second lipid bilayer expanses comprises less than 5 μg.

28. The method of claim 27, wherein each of said first and said second lipid bilayer expanses comprises less than 1 μg.

29. The method of claim 28, wherein each of said first and said second lipid bilayer expanses comprises less than 0.5 μg.

30. The method of claim 22, wherein said substrate comprises between about 10 and about 100 distinct bilayer-compatible surface regions.

31. The method of claim 22, wherein said substrate comprises at least about 2500 distinct bilayer-compatible surface regions.

32. The method of claim 31, wherein said substrate comprises at least about 25,000 distinct bilayer-compatible surface regions.

33. The method of claim 32, wherein said substrate comprises at least about 2.5 million distinct bilayer-compatible surface regions.

34. The method of claim 18, wherein the bilayer-compatible surface regions are separated from one another by bilayer barrier regions that are between about 1 μm and about 10 μm in width.

* * * * *